(12) United States Patent
Slepnev

(10) Patent No.: US 7,445,893 B2
(45) Date of Patent: Nov. 4, 2008

(54) SAMPLING METHOD FOR AMPLIFICATION REACTION ANALYSIS

(75) Inventor: Vladimir I. Slepnev, Newton, MA (US)

(73) Assignee: Primera Biosystems, Inc., Mansfield, MA (US)

( * ) Notice: Subject to any disclaimer, the term of this patent is extended or adjusted under 35 U.S.C. 154(b) by 73 days.

(21) Appl. No.: 10/719,185

(22) Filed: Nov. 21, 2003

(65) Prior Publication Data
US 2004/0166513 A1   Aug. 26, 2004

Related U.S. Application Data

(63) Continuation-in-part of application No. 10/387,286, filed on Mar. 12, 2003, now Pat. No. 7,081,339.

(60) Provisional application No. 60/372,045, filed on Apr. 12, 2002, provisional application No. 60/428,038, filed on Nov. 21, 2002, provisional application No. 60/440,010, filed on Jan. 14, 2003.

(51) Int. Cl.
*C12Q 1/68* (2006.01)
*C12P 19/34* (2006.01)

(52) U.S. Cl. .................................. 435/6; 435/91.2

(58) Field of Classification Search .............. 435/6, 435/91.2
See application file for complete search history.

(56) References Cited

U.S. PATENT DOCUMENTS

| | | | |
|---|---|---|---|
| 5,210,015 A | 5/1993 | Gelfand et al. | 435/6 |
| 5,691,146 A | 11/1997 | Mayrand | 435/6 |
| 6,005,663 A | 12/1999 | Waterhouse et al. | |
| 6,054,035 A | 4/2000 | Kambara | |
| 6,207,031 B1 | 3/2001 | Adourian et al. | |
| 6,221,600 B1 | 4/2001 | MacLeod et al. | 435/6 |
| 6,228,589 B1 * | 5/2001 | Brenner | 435/6 |
| 6,479,235 B1 * | 11/2002 | Schumm et al. | 435/6 |
| 6,482,615 B2 | 11/2002 | Tal et al. | 435/91.2 |
| 6,495,326 B2 | 12/2002 | Kurane et al. | 435/6 |
| 6,531,282 B1 | 3/2003 | Dau et al. | 435/6 |
| 2002/0028452 A1 | 3/2002 | Wittwer et al. | |
| 2002/0146688 A1 | 10/2002 | Masataka | |
| 2002/0160361 A1 | 10/2002 | Loehrlein et al. | |

FOREIGN PATENT DOCUMENTS

| | | |
|---|---|---|
| WO | WO98/33942 | 8/1998 |
| WO | WO00/66995 | 11/2000 |
| WO | WO02/16652 | 2/2002 |
| WO | 2003035841 | 5/2003 |
| WO | WO03/035841 | 5/2003 |
| WO | 2004048528 | 6/2004 |

OTHER PUBLICATIONS

Sanchez-Vega et al., Laboratory Investigation 82(1), 345A (Jan. 2002).*

Sanchez-Vega et al., J. Mol. Diagnostics 4(4), 223-229 (Nov. 2002).*
Li et al., Anal. Bioanal. Chem. 374, 269-273 (Aug.-Sep. 2002).*
International Search Report of International Application No. PCT/US03/37420.
Holland, et al., "Detection of specific polymerase chain reaction product by utilizing the 5'→3' exonuclease activity of *Thermus aquaticus* DNA polymerase", (1991), *Proc. Natl. Acad. Sci. USA*, 88:7276-7280.
Borson, et al., "Direct Quantitation of RNA Transcripts by Competitive Single-Tube RT-PCR and Capillary Electrophoresis", (1998), *Biotechniques*, 25:130-137.
Rajcevic, et al., "Assessment of differential expression of oncogenes in gastric adenocarcinoma by fluorescent multiplex RT-PCR assay", (2001), *Pflugers Arch., Eur. J. Physiol.*, 442 (6 Suppl 1):R190-192.
Odin et al., "Rapid method for relative gene expression determination in human tissues using automated capillary gel electrophoresis and multicolor detection", (1999), *J. Chromatogr. B*, 734:47-53.
George, et al., "Capillary electrophoresis methodology for identification of cancer related gene expression patterns of fluorescent differential display polymerase chain reaction", (1997), *J. Chromatogr. B.*, 695:93-102.
Omori, et al., "Comparative PCR: A Simple and Sensitive Method for Quantifying Low-Abundance mRNA Species", (2000), *Genomics*, 67:140-145.
Wiesner, Rudolf J., "Direct Quantification of Picomolar Concentrations of mRNAs by Mathematical Analysis of a Reverse Transcription/Exponential Polymerase Chain Reaction Assay," Nucleic Acids Research, vol. 20, No. 21, 1992, pp. 5863-5864.
Wiesner, et al., "Counting Target Molecules by Exponential Polymerase Chain Reaction: Copy Number of Mitochondrial DNA in Rat Tissues," Biochemical and Biophysical Research Communications, vol. 183, No. 2, 1992, pp. 553-559.

(Continued)

*Primary Examiner*—Kenneth R. Horlick
(74) *Attorney, Agent, or Firm*—Mark J. FitzGerald; Nixon Peabody LLP

(57) ABSTRACT

The invention provides sampling methods that permit the quantitative analysis of nucleic acid amplification reactions. The methods disclosed permit quantitative expression analysis of multiple genes or transcription units, both in the same amplification reaction and in multiple amplification reactions. In one aspect, the methods disclosed include, briefly, dispensing or withdrawing an aliquot from a reaction mixture at plural stages of an amplification regimen, separating and detecting nucleic acids in the aliquot, determining the quantity of a plurality of separated nucleic acid species in the aliquot, and for each separated nucleic acid species from each stage, correlating the quantity of the species with the stage at which the aliquot comprising the species was dispensed, thereby generating a profile of the amplification.

58 Claims, 6 Drawing Sheets

OTHER PUBLICATIONS

Meldrum Deirdre, "Automation for Genomics, Part One: Preparation for Sequencing," Genome Research, vol. 10, No. 8, 2000, pp. 1081-1092.

Garcia, et al., "Scalable Transcriptional Analysis Routine—Multiplexed Quantitative Real-Time Polymerase Chain Reaction Platform for Gene Expression Analysis and Molecular Diagnostics," Journal of Molecular Diagnostics, vol. 7, No. 4, Oct. 2005, pp. 444-454.

European Search Report, 03783738.2, Jan. 30, 2006.

Belgrader, P. and Marino, M.A., LRA, 9:3-7 (1997). "Automated Sample Processing Using Robotics for Genetic Typing of Short Tandem Repeat Polymorphisms by Capillary Electrophoresis."

* cited by examiner

FIGURE 4
| TARGET 1 | TARGET 2 |
|---|---|
1) ANNEAL AND EXTEND DOWNSTREAM TAGGED PRIMERS
 
2) ANNEAL AND EXTEND UPSTREAM TAGGED PRIMERS
 
3) REPEAT STEPS 1 & 2
 
AND
 
RESULT:
 
4) REMOVE PRIMERS
5) AMPLIFY WITH TAG SPECIFIC PRIMERS T1, T2 (T1 LABELED)
| TARGET 1 | TARGET 2 |
|---|---|
 
 
6) SEPARATE
7) DETECT LABEL ON SEPARATED SPECIES

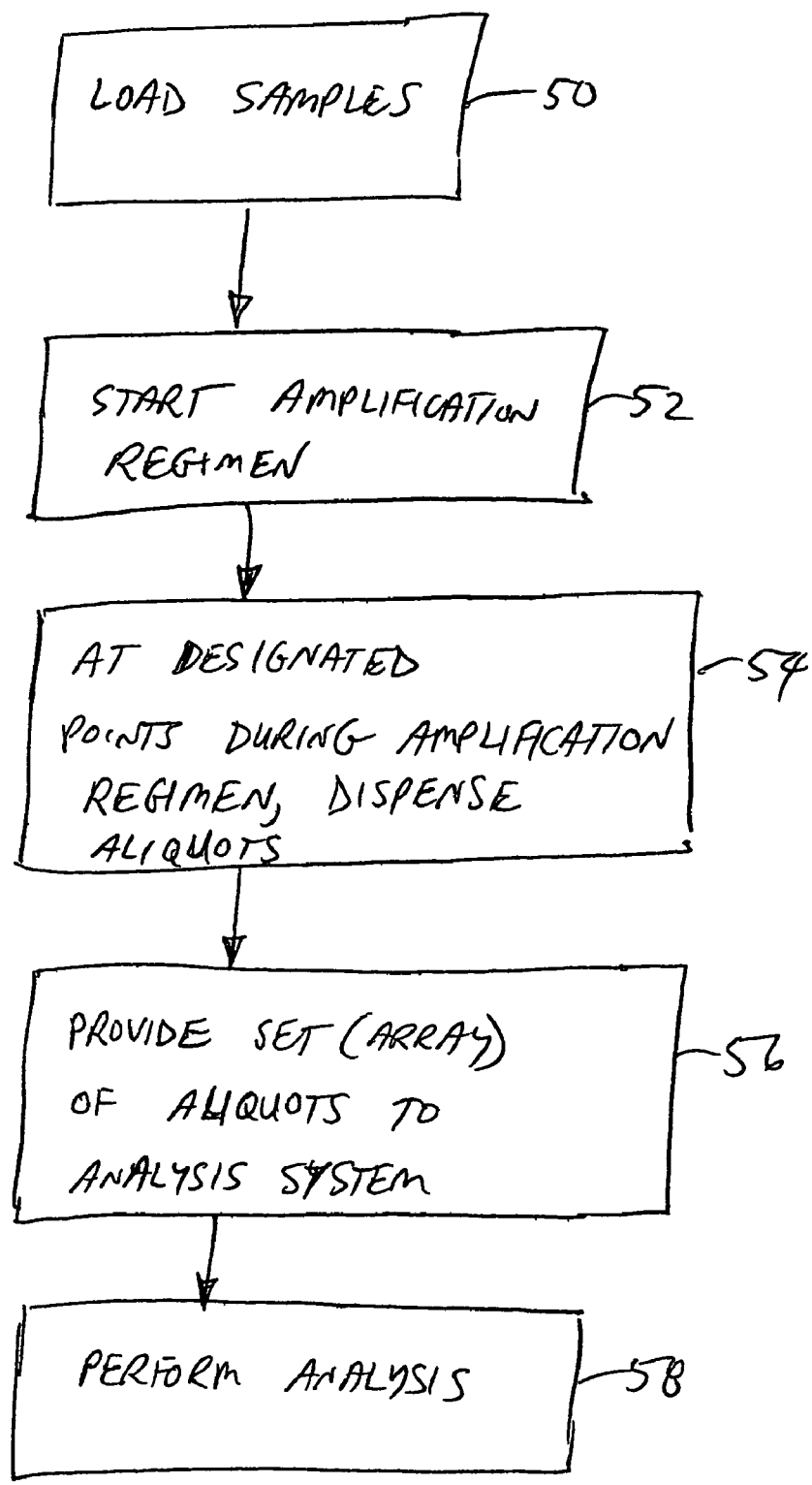

SAMPLING METHOD FOR AMPLIFICATION REACTION ANALYSIS

RELATED APPLICATIONS

This application is a continuation-in-part of U.S. patent application with Ser. No. 10/387,286, filed Mar. 12, 2003, now issued U.S. Pat. No. 7,081,339, which claims priority to U.S. provisional application 60/372,045, filed Apr. 12, 2002, the entirety of which is hereby incorporated by reference. The present application also claims priority under 35 U.S.C. 119 (c) to U.S. Provisional Application Nos. 60/428,038, filed Nov. 21, 2002; and 60/440,010, filed Jan. 14, 2003, the entirety of each is hereby incorporated by reference.

FIELD OF THE INVENTION

Aspects of the invention relate to sampling methods for nucleic acid amplification reactions. Such sampling methods find use in deriving quantitative information from nucleic acid amplification analyses, for example, transcriptional profiling analysis.

BACKGROUND

Nucleic acid probe technology has developed rapidly in recent years as researchers have discovered its value for detection of various diseases, organisms or genetic features which are present in small quantities in a human or animal test sample.

A targeted nucleic acid sequence in an organism or cell may be only a very small portion of the entire DNA molecule so that it is very difficult to detect its presence using most labeled DNA probes. Much research has been carried out to find ways to detect only a few molecules of a targeted nucleic acid.

A significant advance in the art is described in U.S. Pat. Nos. 4,683,195; 4,683,202; and 4,965,188. These patents describe amplification and detection methods wherein primers are hybridized to the strands of a targeted nucleic acid (considered the templates) in the presence of a nucleotide polymerization agent (such as a DNA polymerase) and deoxyribonucleoside triphosphates. Under specified conditions, the result is the formation of primer extension products as nucleotides are added along the templates from the 3'-end of the primers. These products are then denatured and used as templates for more of the same primers in another extension reaction. When this cycle of denaturation, hybridization and primer extension is carried out a number of times (for example 25 to 30 cycles), the process which is known as "polymerase chain reaction" exponentially increases the original amount of targeted nucleic acid so that it is readily detected.

Once the targeted nucleic acid has been sufficiently amplified (that is, many times more copies of the molecule have been made), various detection procedures can be used to detect it. The patents noted above, for example, describe the use of insolubilized or detectably labeled probes and gel electrophoresis as representative detection methods.

A wide range of times and temperatures for amplification methods are generally described, with the specific combination of time and temperature largely dependent upon the type of DNA polymerase used, the complexity of the mixture of nucleic acids including the targeted nucleic acid, the length and specificity of the primers, the length of the targeted nucleic acid, pH and several other reaction conditions and components.

Amplification reactions have been used for a number of applications, for example, in transcription profiling. Transcription profiling promises to impact upon the process of target identification and validation in accelerating the pace of drug discovery, as well as disease diagnosis and prognosis. This method compares expression of genes in a specific situation: for example, between diseased and normal cells, between control and drug-treated cells or between cells responding to treatment and those resistant to it. The information generated by this approach may directly identify specific genes to be targeted by a therapy, and, importantly, reveals biochemical pathways involved in disease and treatment. In brief, it not only provides biochemical targets, but at the same time, a way to assess the quality of these targets. Moreover, in combination with cell-based screening, transcription profiling is positioned to dramatically change the field of drug discovery. Historically, screening for a potential drug was successfully performed using phenotypic change as a marker in functional cellular system. For example, growth of tumor cells in culture was monitored to identify anticancer drugs. Similarly, bacterial viability was used in assays aimed at identifying antibiotic compounds. Such screens were typically conducted without prior knowledge of the targeted biochemical pathway. In fact, the identified effective compounds revealed such pathways and pointed out the true molecular target, enabling subsequent rational design of the next generations of drugs.

Modern tools of transcription profiling can be used to design novel screening methods that will utilize gene expression in place of phenotypic changes to assess the effectiveness of a drug. For example, such methods are described in U.S. Pat. Nos. 5,262,311; 5,665,547; 5,599,672; 5,580,726; 6,045,988 and 5,994,076, as well as in Luehrsen et al. (1997, Biotechniques, 22:168-74), and in Liang and Pardee (1998, Mol Biotechnol. 10:261-7). This approach will be invaluable for drug discovery in the field of central nervous system (CNS) disorders such as dementia, mild cognitive impairment, depression, etc., where phenotypic screening is inapplicable, but a desired transcription profile can be readily established and linked to particular disorders. Once again, the identified effective compounds will reveal the underlying molecular processes. In addition, this method can be instrumental for the development of improved versions of existent drugs, which act at several biochemical targets at the same time to generate the desired pharmacological effect. In such case the change in the transcriptional response may be a better marker for drug action than selection based on optimization of binding to multiple targets.

A number of advanced methods of transcription profiling are based on technology using DNA microarrays, for example, as reviewed in Greenberg, 2001 Neurology 57:755-61; Wu, 2001, J Pathol. 195:53-65; Dhiman et al., 2001, Vaccine 20:22-30; Bier et al., 2001 Fresenius J Anal Chem. 371:151-6; Mills et al., 2001, Nat Cell Biol. 3:E175-8; and as described in U.S. Pat. Nos. 5,593,839; 5,837,832; 5,856,101; 6,203,989; 6,271,957; and 6,287,778. DNA microarray analysis is a method which provides simultaneous comparison of the expression of several thousand genes in a given sample by assessing the hybridization of labeled polynucleotide samples, obtained by reverse transcription of mRNAs, to the DNA molecules attached to the surface of the test array.

One of the most sought after benefits believed possible with the sensitivity of nucleic acid amplification technology is the reliable quantitation of the amount of template present in a sample before amplification. Such a method finds direct application in, for example, transcription profiling. The high sensitivity and fidelity of the amplification reactions makes it possible to extrapolate the original template abundance from the amount of amplification products generated. However, the kinetics of amplification vary with respect to template and stage of the amplification process, making it difficult to fully realize the quantitative potential of nucleic acid amplification procedures.

In order to obtain data that reliably reflect the amount of original template, it is necessary to collect quantitative data at a point in which every target sequence is in the exponential phase of amplification (since it is only in this phase that amplification is extremely reproducible and accurately reflects the abundance of template molecules prior to amplification). Analysis of reactions during exponential phase at a given cycle number should theoretically provide several orders of magnitude of dynamic range. However, low abundance targets will often be below the limit of detection at a set cycle number, while abundant targets will be past the exponential phase. In practice, a dynamic range of 2-3 logs can be quantitated during end-point relative PCR. In order to extend this range, replicate reactions may be performed for a greater or lesser number of cycles, so that all of the samples can be analyzed in the exponential phase.

Holland et al. (1991, Proc. Natl. Acad. Sci. U.S.A. 88: 7276-7280), U.S. Pat. No. 5,210,015 and others have disclosed fluorescence-based approaches to provide real time measurements of amplification products during PCR. Such approaches have either employed intercalating dyes (such as ethidium bromide) to indicate the amount of double-stranded DNA present or they have employed probes containing fluorescence-quencher pairs (also referred to as the "Taq-Man" approach) where the probe is cleaved during amplification to release a fluorescent molecule the concentration of which is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear.

The Taq-Man approach uses an oligonucleotide probe containing a reporter molecule-quencher molecule pair that specifically anneals to a region of a target polynucleotide "downstream", i.e. in the direction of extension of primer binding sites. The reporter molecule and quencher molecule are positioned on the probe sufficiently close to each other such that whenever the reporter molecule is excited, the energy of the excited state nonradiatively transfers to the quencher molecule where it either dissipates nonradiatively or is emitted at a different emission frequency than that of the reporter molecule. During strand extension by a DNA polymerase, the probe anneals to the template where it is digested by the 5' to 3' exonuclease activity of the polymerase. As a result of the probe being digested, the reporter molecule is effectively separated from the quencher molecule such that the quencher molecule is no longer close enough to the reporter molecule to quench the reporter molecule's fluorescence. Thus, as more and more probes are digested during amplification, the number of reporter molecules in solution increases, thus resulting in an increasing number of unquenched reporter molecules which produce a stronger and stronger fluorescent signal.

The other most commonly used real time PCR approach uses the so-called "molecular beacons" technology. This approach is also based upon the presence of a quencher-fluorophore pair on an oligonucleotide probe. In the beacon approach, a probe is designed with a stem-loop structure, and the two ends of the molecule are labeled with a fluorophore and a quencher of that fluorophore, respectively. In the absence of target polynucleotide, the complementary sequences on either end of the molecule permit stem formation, bringing the labeled ends of the molecule together, so that fluorescence from the fluorophore is quenched. In the presence of the target polynucleotide, which bears sequence complementary to the loop and part of the stem structure of the beacon probe, the intermolecular hybridization of the probe to the target is energetically favored over intramolecular stem-loop formation, resulting in the separation of the fluorophore and the quencher, so that fluorescent signal is emitted upon excitation of the fluorophore. The more target present, the more probe hybridizes to it, and the more fluorophore is freed from quenching, providing a read out of the amplification process in real time.

Capillary electrophoresis has been used to quantitatively detect gene expression. Rajevic at el. (2001, Pflugers Arch. 442(6 Suppl 1):R190-2) discloses a method for detecting differential expression of oncogenes by using seven pairs of primers for detecting the differences in expression of a number of oncogenes simultaneously. Sense primers were 5' end-labelled with a fluorescent dye and multiplex fluorescent RT-PCR results were analyzed by capillary electrophoresis on an ABI-PRISM 310 Genetic Analyzer. Borson et al. (1998, Biotechniques 25:130-7) describes a strategy for dependable quantitation of low-abundance mRNA transcripts based on quantitative competitive reverse transcription PCR (QC-RT-PCR) coupled to capillary electrophoresis (CE) for rapid separation and detection of products. George et al., (1997, J. Chromatogr. B. Biomed. Sci. Appl. 695:93-102) describes the application of a capillary electrophoresis system (ABI 310) to the identification of fluorescent differential display-generated EST patterns. Odin et al. (1999, J. Chromatogr. B. Biomed. Sci. Appl. 734:47-53) describes an automated capillary gel electrophoresis with multicolor detection for separation and quantification of PCR-amplified cDNA.

SUMMARY OF THE INVENTION

Real time amplification methods are provided that monitor the abundance of one or more amplification products at multiple points during the amplification regimen. A sampling method withdraws or extrudes aliquots from the amplification reaction mixture during the amplification regimen. Quantitative analysis can then be preformed on the sampled nucleic acid amplification reactions. Quantitative information garnered during an amplification regimen can be used to develop a detailed amplification profile that in turn permits the reliable determination of original template abundance.

The present invention provides a method of monitoring the amplification of a nucleic acid sequence, the method comprising: providing a nucleic acid amplification reaction mixture comprising a template of the nucleic acid sequence; performing an amplification regimen on the mixture; automatically dispensing an aliquot of the reaction mixture at plural stage intervals throughout the amplification regimen; separating and detecting the nucleic acid species in the aliquot; and, for respective ones of plural separated species, determining the quantity of separated nucleic acid in the aliquot.

The present invention also provides a method of determining the transcription profile of a nucleic acid sequence, the method comprising: providing a nucleic acid amplification reaction mixture; performing an amplification regimen on the mixture; dispensing an aliquot of the reaction mixture at plural stage intervals throughout the amplification regimen; separating and detecting the nucleic acid species in the aliquot; and, for respective ones of plural separated species, determining the quantity of separated nucleic acid in the aliquot; and determining the transcription profile of the nucleic acid sequence.

The invention encompasses a method of analyzing a nucleic acid amplification comprising:
provm a nucleic acid amplification reaction mixture comprising a plurality of different amplification templates;
subjecting the reaction mixture to an amplification regimen;
dispensing or withdrawing an aliquot from the reaction mixture at plural stages during the amplification regimen;
separating and detecting nucleic acids in the aliquot;
determining the quantity of a plurality of separated nucleic acid species in the aliquot; and
for each separated nucleic acid species from each stage, correlating the quantity of the species with the stage at which the aliquot comprising the species was dispensed, wherein the correlating generates an amplification profile of the nucleic acid amplification.

In one embodiment, the plurality of different amplification templates comprises at least three different amplification templates.

In another embodiment, the plurality of different amplification templates comprises at least five different amplification templates.

In another embodiment, the plurality of different amplification templates comprises at least ten different amplification templates.

In another embodiment, the plurality of different amplification templates comprises at least 20 different amplification templates.

In another embodiment, the plurality of different amplification templates comprises at least 50 different amplification templates.

In another embodiment, the plurality of different amplification templates comprises at least 100 different amplification templates.

In another embodiment, the plurality of different amplification templates comprises at least 200 different amplification templates.

In another embodiment, a plurality of amplification reaction mixtures is subjected to the method. In another embodiment, the plurality of amplification reaction mixtures is subjected to the method simultaneously.

In another embodiment, the method generates an amplification profile for a plurality of amplified nucleic acid species.

In another embodiment, the amplification profile provides quantitative information regarding the abundance of a nucleic acid species present in the nucleic acid amplification reaction mixture at the start of the amplification regimen.

In another embodiment, the amplification profile is a transcriptional profile.

In another embodiment, the nucleic acid amplification regimen comprises thermal cycling.

In another embodiment, the nucleic acid amplification regimen comprises isothermal cycling.

In another embodiment, the nucleic acid amplification regimen comprises PCR.

In another embodiment, the nucleic acid amplification regimen comprises a method selected from the group consisting of ligase-mediated amplification, NASBA, and rolling circle amplification.

In another embodiment, the aliquot is dispensed into a receptacle having a plurality of aliquot-receiving sites. In one embodiment, the receptacle is a multiwell plate. In another embodiment, the receptacle comprises a plurality of CE capillaries.

In another embodiment, the aliquot is dispensed into or onto a receptacle capable of holding a plurality of aliquots without mixing among the aliquots.

In another embodiment, the amplification regimen is cyclic. In another embodiment, the dispensing or withdrawing is performed after each of a plurality of cycles. In another embodiment, the dispensing or withdrawing is performed after every cycle in the regimen.

In another embodiment, the separating comprises electrophoresis.

In another embodiment, the separating comprises capillary electrophoresis.

In another embodiment, the separating comprises liquid chromatography.

In another embodiment, the detecting comprises detection of one or more fluorescent labels.

In another embodiment, the detecting comprises mass spectrometry.

In another embodiment, the amplification regimen is performed in a container, and the aliquot dispensing is performed by withdrawing the aliquot from the container. In another embodiment, the container is a well or a test tube.

In another embodiment, the amplification regimen is performed in a container, and the dispensing is performed by extruding the aliquot from the container.

In another embodiment, the amplification regimen is performed in a container with openings at one or both ends. In another embodiment, the container is a capillary tube.

The invention further encompasses a method of analyzing the expression of a plurality of RNA transcripts between first and second gene expressing entities, the method comprising
providing a first nucleic acid amplification reaction mixture, the mixture comprising a plurality of different amplification templates, wherein the amplification templates comprise reverse transcription products from a plurality of RNA transcripts from a first gene expressing entity;
providing a second nucleic acid amplification reaction mixture, the mixture comprising a plurality of different amplification templates, wherein the amplification templates comprise reverse transcription products from a plurality of RNA transcripts from a second gene expressing entity;
subjecting the reaction mixtures to an amplification regimen;
dispensing or withdrawing an aliquot from the first and the second reaction mixtures at plural stages during the amplification regimen;
separating and detecting nucleic acids in the aliquot;
determining the quantity of a plurality of separated nucleic acid species in the aliquot;
for each separated nucleic acid species from each stage, correlating the quantity of the species with the stage at which the aliquot comprising the species was dispensed, thereby generating a transcriptional profile of the plurality of RNA transcripts expressed by the first and the second gene expressing entities; and
comparing the transcriptional profile from the first gene expressing entity with the transcriptional profile from the second gene expressing entity.

In one embodiment, the plurality of RNA transcripts comprises at least three different RNA transcripts.

In another embodiment, the plurality of RNA transcripts comprises at least five different RNA transcripts.

In another embodiment, the plurality of RNA transcripts comprises at least ten different RNA transcripts.

In another embodiment, the plurality of RNA transcripts comprises at least 20 different RNA transcripts.

In another embodiment, the plurality of RNA transcripts comprises at least 50 different RNA transcripts.

In another embodiment, the plurality of RNA transcripts comprises at least 100 different RNA transcripts.

In another embodiment, the plurality of RNA transcripts comprises at least 200 different RNA transcripts.

In another embodiment, the amplification regimen is cyclic. In another embodiment, the nucleic acid amplification regimen comprises thermal cycling. In another embodiment, the nucleic acid amplification regimen comprises isothermal cycling. In another embodiment, the nucleic acid amplification regimen comprises PCR. In another embodiment, the nucleic acid amplification regimen comprises a method selected from the group consisting of ligase-mediated amplification, NASBA, and rolling circle amplification.

In another embodiment, the aliquot is dispensed into a receptacle having a plurality of aliquot-receiving sites. In another embodiment, the receptacle is a multiwell plate. In another embodiment, the receptacle comprises a plurality of CE capillaries.

In another embodiment, the aliquot is dispensed into or onto a receptacle capable of holding a plurality of aliquots without mixing among the aliquots.

In another embodiment, the dispensing or withdrawing is performed after a plurality of cycles.

In another embodiment, the dispensing or withdrawing is performed after every cycle in the regimen.

In another embodiment, the separating comprises electrophoresis.

In another embodiment, the separating comprises capillary electrophoresis.

In another embodiment, the separating comprises liquid chromatography.

In another embodiment, the detecting comprises detection of one or more fluorescent labels.

In another embodiment, the detecting comprises mass spectrometry.

In another embodiment, the amplification regimen is performed in a container, and the aliquot dispensing is performed by withdrawing the sample from the container.

In another embodiment, the container is a well or a test tube.

In another embodiment, the amplification regimen is performed in a container, and wherein the dispensing is performed by extruding the aliquot from the container.

In another embodiment, the container is a capillary tube.

BRIEF DESCRIPTION OF THE DRAWINGS

FIG. 4 is a schematic diagram of an amplification method wherein a plurality of differently-sized targets is amplified in a single reaction with a single pair of amplification primers.

FIG. 6 is a flow chart of a process that may be performed by the apparatus shown in FIG. 5. In an act 50, samples are loaded into the reaction chamber. In act 52, an amplification regimen is started. In act 54, at designated points during the amplification regimen, the aliquots are dispensed (automatically, in the illustrated embodiment) for subsequent analysis by analysis system. At act 56, the aliquots are provided to the analysis system. Such dispensed samples may be analyzed right away or they may be set aside for batch processing once all the sets of intermediate (mid-amplification regimen) aliquots are obtained and after the regimen is complete. At act 58, the samples are analyzed.

DETAILED DESCRIPTION OF THE INVENTION

Definitions

Figure 1:
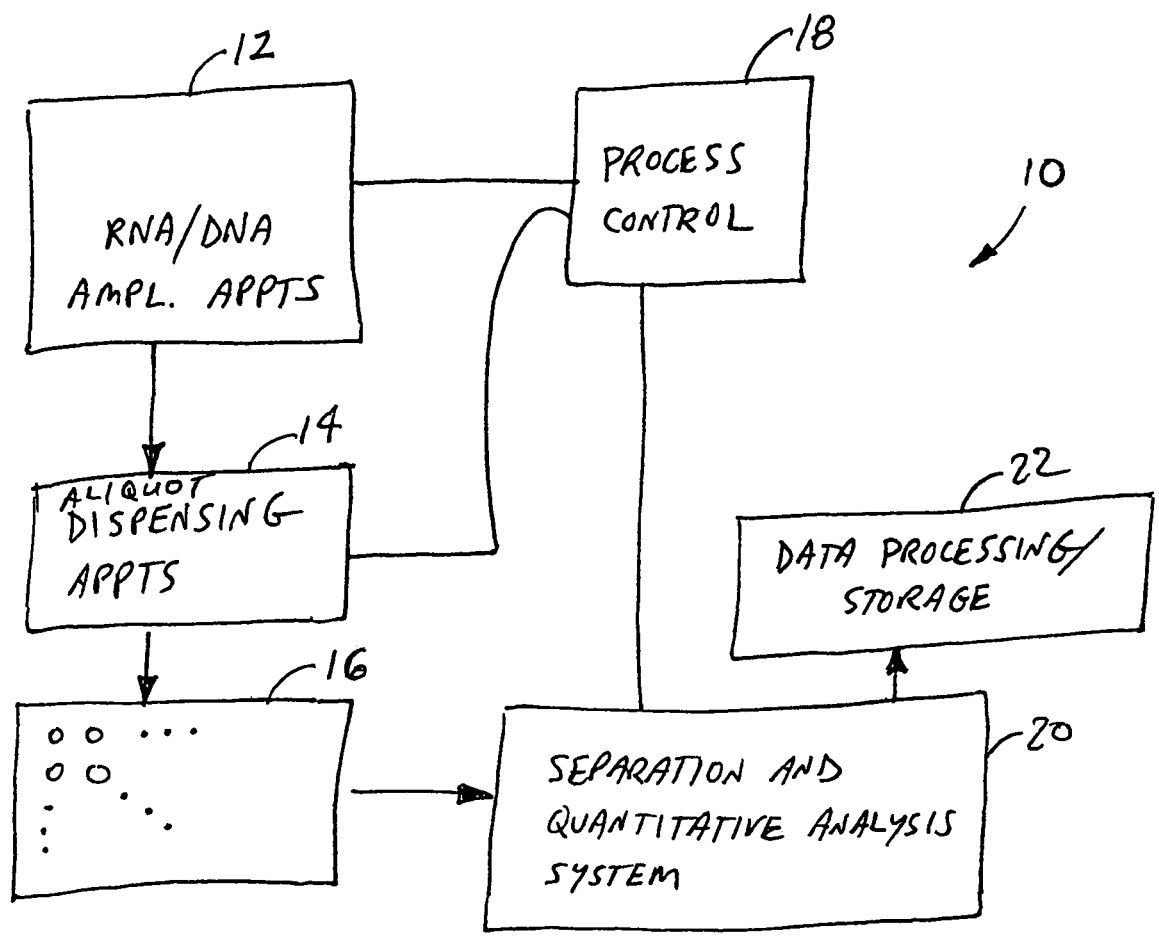
FIG. 1 shows a block diagram of a system for amplification profiling.

As used herein, the term "sample" refers to a biological material which is isolated from its natural environment and containing a polynucleotide. A "sample" according to the invention may consist of purified or isolated polynucleotide, or it may comprise a biological sample such as a tissue sample, a biological fluid sample, or a cell sample comprising a polynucleotide. A biological fluid includes blood, plasma, sputum, urine, cerebrospinal fluid, lavages, and leukophoresis samples. A sample of the present invention can comprise any plant, animal, bacterial or viral material containing a polynucleotide.

As used herein, a "polynucleotide molecule derived from a specific sample" may be a polynucleotide isolated from a specific sample, or it may be a polynucleotide synthesized from a specific sample, e.g., through the technologies of reverse transcription (RT) or polymerase chain reaction (PCR), ligase chain reaction (LCR), nucleic acid sequence based amplification (NASBA), strand displacement amplification (SDA), and any other nucleic acid amplification technologies known in the art.

As used herein, the term "amplification profile" or the equivalent terms "amplification curve" and "amplification plot" mean a mathematical curve representing the signal from a detectable label incorporated into a nucleic acid sequence of interest at two or more steps in an amplification regimen, plotted as a function of the cycle number or stage at which the samples were withdrawn or extruded. The amplification profile is preferably generated by plotting the fluorescence of each band detected after capillary electrophoresis separation of nucleic acids in individual reaction samples. Most commercially available fluorescence detectors are interfaced with software permitting the generation of curves based on the signal detected.

As used herein, the term "aliquot" refers to a sample volume taken from a prepared reaction mixture. The volume of an aliquot can vary, but will generally be constant within a given experimental run. An aliquot will be less than the volume of the entire reaction mixture. Where there are X aliquots to be withdrawn during an amplification regimen, the volume of an aliquot will be less than or equal to 1/X times the reaction volume.

As used herein, the term "dispense" means dispense, transfer, withdraw, extrude or remove.

As used herein, the term "reaction chamber" refers to a fluid chamber for locating reactants undergoing or about to undergo a reaction (e.g., an amplification reaction or an extraction process). A "reaction chamber" may be comprised of any suitable material that exhibits minimal non-specific adsorptivity or is treated to exhibit minimal non-specific adsorptivity, for example, including, but not limited to, glass, plastic, nylon, ceramic, or combinations thereof.

As used herein, the term "amplified product" refers to polynucleotides which are copies of all or a portion of a particular polynucleotide sequence and/or its complementary sequence, which correspond in nucleotide sequence to a template polynucleotide sequence and its complementary sequence. An "amplified product," according to the invention, may be DNA or RNA, and it may be double-stranded or single-stranded.

As used herein, the terms "synthesis" and "amplification" are used interchangeably to refer to a reaction for generating a copy of a particular polynucleotide sequence or for increasing the copy number or amount of a particular polynucleotide sequence. It may be accomplished, without limitation, by the in vitro methods of polymerase chain reaction (PCR), ligase chain reaction (LCR), nucleic acid sequence based amplification (NSBA), strand displacement amplification, or any other method known in the art. For example, polynucleotide amplification can be a process using a polymerase and a pair of oligonucleotide primers for producing any particular polynucleotide sequence, i.e., the target polynucleotide sequence or target polynucleotide, in an amount which is greater than that initially present.

As used herein, a "target polynucleotide" is a polynucleotide sequence whose abundance in a biological sample is to be analyzed. A target polynucleotide may be isolated or amplified before its expression level is analyzed. For example, a target polynucleotide may be a sequence that lies between the hybridization regions of two members of a pair of oligonucleotide primers which are used to amplify it. A target polynucleotide may be RNA or DNA, for example, it may be mRNA or cDNA, a coding region of a gene or a portion thereof. A target polynucleotide sequence generally exists as part of a larger "template" sequence; however, in some cases, a target sequence and the template are the same. Although "template sequence" generally refers to the polynucleotide sequence initially present prior to amplification, the products from an amplification reaction may also be used as template sequence in subsequent amplification reactions. A "target polynucleotide" or a "template sequence" may be a normal polynucleotide (e.g., wild type) or a mutant polynucleotide that is or includes a particular sequence.

As used herein, an "oligonucleotide primer" refers to a polynucleotide molecule (i.e., DNA or RNA) capable of annealing to a polynucleotide template and providing a 3' end to produce an extension product which is complementary to the polynucleotide template. The conditions for initiation and extension usually include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer according to the invention may be single- or double-stranded. The primer is single-stranded for maximum efficiency in amplification, and the primer and its complement form a double-stranded polynucleotide. But it may be double-stranded. "Primers" in specific embodiments of the methods described are less than or equal to 100 nucleotides in length, e.g., less than or equal to 90, or 80, or 70, or 60, or 50, or 40, or 30, or 20, or 15, or equal to 10 nucleotides in length.

As used herein, a "polynucleotide" generally refers to any polyribonucleotide or poly-deoxyribonucleotide, which may be unmodified RNA or DNA or modified RNA or DNA. "Polynucleotides" include, without limitation, single- and double-stranded polynucleotides. As used herein, the term "polynucleotide(s)" also includes DNAs or RNAs as described above, that contain one or more modified bases. Thus, DNAs or RNAs with backbones modified for stability or for other reasons are "polynucleotides". The term "polynucleotides" as it is used herein embraces such chemically, enzymatically or metabolically modified forms of polynucleotides, as well as the chemical forms of DNA and RNA characteristic of viruses and cells, including for example, simple and complex cells. A polynucleotide useful for the present invention may be an isolated or purified polynucleotide or it may be an amplified polynucleotide in an amplification reaction.

As used herein, "isolated" or "purified" when used in reference to a polynucleotide means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95%, up to 99-100% pure) of non-nucleotide or polynucleotide material naturally associated with it, and thus is distinguished from isolated chromosomes.

As used herein, the term "cDNA" refers to complementary or copy polynucleotide produced from an RNA template by the action of RNA-dependent DNA polymerase (e.g., reverse transcriptase). A "cDNA clone" refers to a duplex DNA sequence complementary to an RNA molecule of interest, carried in a cloning vector.

As used herein, "genomic DNA" refers to chromosomal DNA, as opposed to complementary DNA copied from an RNA transcript. "Genomic DNA", as used herein, may be all of the DNA present in a single cell, or may be a portion of the DNA in a single cell.

The term "expression" refers to the production of a protein or nucleotide sequence in a cell or in a cell-free system, and includes transcription into an RNA product, post-transcriptional modification and/or translation into a protein product or polypeptide from a DNA encoding that product, as well as possible post-translational modifications.

As used herein, the term "gene expressing entities" refers to a cell, a tissue, or an organism that expresses one or more genes as RNA transcripts. The term also encompasses entities that are not comprised by a cell, a tissue or an organism, but that nonetheless produce RNA transcripts from a nucleic acid template, for example, an in vitro transcription reaction.

As used herein, the term "expression profile" or "transcriptional profile" refers to a representation of the quantitative (i.e., abundance) and qualitative expression of one or more genes in a sample. Preferably the transcriptional profile describes the activity of multiple (i.e., at least 3, preferably at least 5, 10, 15, 20, 30, 50, 100, 200, 500, 1000, 10,000 or more) genes or transcription units in a sample. A transcriptional profile for a biological sample can be assembled from the nucleic acid amplification profiles from one or more amplification regimens.

As used herein, the term "comparing the transcriptional profile" refers to comparing the differential expression of one or more polynucleotides in two or more samples. Comparison can be between the overall pattern of expression, including the presence, absence and/or abundance of individual amplicons or sets of amplicons. Comparison can be manual or automated.

As used herein, the term "abundance" refers to the amount (e.g., measured in μg, μmol or copy number) of a target polynucleotide in a sample. The "abundance" of a polynucleotide may be measured by methods well known in the art (e.g., by UV absorption, by comparing band intensity on a gel with a reference of known length and amount), for example, as described in *Basic Methods in Molecular Biology*, (1986, Davis et al., Elsevier, N.Y.); and *Current Protocols in Molecular Biology* (1997, Ausubel et al., John Wiley & Sons, Inc.). One way of measuring the abundance of a polynucleotide in the present invention is to measure the fluorescence intensity emitted by such polynucleotide, and compare it with the fluorescence intensity emitted by a reference polynucleotide, i.e., a polynucleotide with a known amount.

As used herein, the term "sampling device" refers to a mechanism that withdraws or extrudes an aliquot from an amplification during the amplification regimen. Sampling devices in the embodiments herein are adapted to minimize contamination of the amplification reaction(s), by, for example, using pipeting tips or needles that are either disposed of after a single sample is withdrawn, or by incorporating one or more steps of washing the needle or tip after each sample is withdrawn. Alternatively, the sampling device can contact the capillary to be used for capillary electrophoresis directly with the amplification reaction in order to load an aliquot into the capillary. Alternatively, the sample device can include a fluidic line (e.g. a tube) connected to a controllable valve which will open at a particular cycle or point in the amplification regimen. Sampling devices known in the art include, for example, the multipurpose Robbins Scientific Hydra 96 pipettor, which is adapted to sampling to or from 96 well plates. This and others can be readily adapted for use according to the methods of the invention.

As used herein, the term "robotic arm" means a device, preferably controlled by a microprocessor, that physically transfers samples, tubes, or plates containing samples from one location to another. Each location can be a unit in a modular apparatus. An example of a robotic arm useful according to the invention is the Mitsubishi RV-E2 Robotic Arm. Software for the control of robotic arms is generally available from the manufacturer of the arm.

As used herein, the term "multiwell plate" refers to a receptacle comprising multiple (e.g., at least two, but often 5, 8, 12, 24, 36, 96, or 384) discrete sites for the deposition and holding of a liquid sample. The sites can be depressions or wells formed in or on a piece of plastic or similar material, and are preferably arranged in a regular pattern, e.g., in a grid (a 96 well plate, for example, will comprise a rectangular grid of 8 wells in one dimension and 12 wells in the other. It is noted that aliquots of amplification reactions can also be deposited on a flat surface (i.e., one without depressions or wells) as long as they are deposited such that there is no mixing among the deposited aliquots.

As used herein, the term "amplification templates" refers to a nucleic acid that can act as a template for the enzymatic polymerization of a complementary strand. Amplification templates can comprise DNA, RNA and PNA, and can be double or single stranded.

As used herein, the term "amplification regimen" means a process of specifically amplifying the abundance of a nucleic acid sequence of interest. Amplification regimens are most often "cyclic," i.e., they are comprised of repeated steps of primer annealing and polymerization, usually in conjunction with repeated steps of thermal denaturation of template nucleic acids. A cyclic amplification regimen will preferably comprise at least two, and preferably at least 5, 10, 15, 20, 25, 30, 35 or more iterative cycles of thermal denaturation, oligonucleotide primer annealing to template molecules, and nucleic acid polymerase extension of the annealed primers. Conditions and times necessary for each of these steps are well known in the art. Amplification achieved using an amplification regimen is preferably exponential, but can alternatively be linear. Other amplification regimens are non-cyclic, or continuous. Non-cyclic amplifications proceed to completion once initiated, and most often involve templates with RNA polymerase recognition sites and the action of RNA polymerase and reverse transcriptase.

As used herein, the term "thermal cycled amplification regimen" refers to an amplification regimen comprising a plurality of cycles of thermal denaturation, primer annealing and primer extension or polymerization.

As used herein, the term "isothermal" when applied to an amplification regimen means that the amplification, once initiated, proceeds at a single temperature, without need for cycles involving thermal denaturation of template nucleic acids.

As used herein, the phrase "dispensing an aliquot from the reaction mixture at plural stages" refers to the withdrawal or extrusion of an aliquot at least twice, and preferably at least 3, 4, 5, 10, 15, 20, 30 or more times during an amplification regimen. A "stage" will refer to a point after a given number of cycles, or, where the amplification regimen is non-cyclic, will refer to a selected time after the initiation of the regimen.

As used herein, the term "extrude" means that an aliquot is forced out of one end or orifice of a reaction vessel by pressure, e.g., air pressure, applied on another end or orifice of the vessel.

As used herein, the term "quantitative information regarding the abundance of a nucleic acid species" refers to information about the amount of a nucleic acid species. The quantitative information can be relative (e.g., fold difference over the amount of that nucleic acid in another sample), or absolute.

DESCRIPTION OF THE PREFERRED EMBODIMENTS

The present invention is directed to sampling methods for quantitatively monitoring and analyzing the amplification of polynucleotides. While the most frequently used nucleic acid amplification method is thermal cycling PCR, the methods disclosed herein find application not only in PCR, but also in any nucleic acid amplification protocol, most particularly, but not limited to, those that involve repeated cycles of nucleic acid synthesis. Continuous methods, such as the RNA polymerase/reverse transcriptase mediated methods (e.g., 3SR or NASBA, see below) can also benefit from the sampling methods described herein, by, for example, removing samples at given times during the amplification process.

A basic PCR amplification can be broken down into three phrases: (1) exponential phase: exact doubling of product is accumulated at every cycle, assuming 100% reaction efficiency. The reaction is very specific and precise; (2) Linear (high variability) phase: the reaction components are being consumed, the reaction is slowing and the products are starting to degrade; (3) plateau (end-point) phase: the reaction has stopped, no more products are being made and if left long enough, the PCR products will begin to degrade. The problem with detection in the plateau phase of PCR is that the quantitation is affected so as to no longer reflect the amount of the starting nucleic acid template.

"Real-time PCR" analysis detects specific nucleic acid amplification products as they accumulate in real-time. Real-time PCR provides advantages over traditional end-point PCR by allowing for the detection of PCR amplification during the early phases of the reaction.

Nucleic acid amplification profiling involves the measurement of amplification products present at various stages during an amplification regimen. Because it can identify the limits of the exponential, linear and plateau phases of an amplification reaction, knowledge of the abundance of amplification product at various stages of the amplification process permits one to reliably extrapolate the abundance of the original template in a biological sample. While an amplification profile of a single nucleic acid template or a small set of such templates can be generated through use of the TaqMan™ or "molecular beacons"-type real time approaches, these methods are rather limited in the number of targets that can be followed in a single reaction. A major limitation is that each different species must be labeled with a differentially detectable fluorophore.

U.S. patent application with Ser. No. 60/372,045 describes a real-time PCR method using capillary electrophoresis for analysis (the entirety of which is incorporated herein by reference). The Patent application provides a method for monitoring the amplification of a nucleic acid sequence of interest, the method comprising: (a) contacting a nucleic acid sample with a first and a second oligonucleotide primer, wherein the first oligonucleotide primer specifically hybridizes with a nucleic acid molecule comprising the nucleic acid sequence of interest, and the second oligonucleotide primer specifically hybridizes with the complementary strand of the nucleic acid sequence of interest, wherein the primer extension product of one oligonucleotide primer, when separated from its complement, can serve as a template for the synthesis of the extension product of the other primer, and wherein at least one of the first and the second primers is labeled and preferably, labeled with a detectable marker; (b) subjecting the mixture resulting from step (a) to an amplification regimen, the regimen comprising at least two cycles of nucleic acid strand separation, oligonucleotide primer annealing, and polymerase extension of annealed primers; and (c) removing an aliquot of the mixture, separating nucleic acid molecules in the aliquot, and detecting incorporation of the at least one detectable marker, wherein the removing is performed during the cycling regimen of step (b), and wherein the detection permits the monitoring of the amplification in real time. Data analysis, including standard curve generation and copy number calculation, can be performed automatically.

The sampling method disclosed herein permits the removal or extrusion of samples from an amplification reaction at various cycles during the amplification process. By withdrawing or extruding samples of the reaction mixture at various cycles of the amplification regimen and detecting the size and amount of various amplified species present, the amount of numerous amplified products can be monitored at each phase of the amplification, thereby identifying the limits of the exponential, linear and plateau phases for a target sequence in a reaction mixture. This approach can be optimally applied to amplification methods that permit the multiplex amplification of greater numbers of target sequences in a single reaction vessel. By highlighting the exponential phase for the amplification of each different template species present in a biological sample, this approach permits the accurate extrapolation of the amounts of numerous templates present in a biological sample. Thus, the sampling method, alone or particularly in combination with methods that increase the multiplex ability of amplification reactions, provides a dramatic increase in the amount of quantitative template information one can obtain from a single amplification reaction. When the initial biological sample contains mRNA and the amplification process amplifies the mRNA or a DNA copy of it, the amplification profile is useful to quantitate the abundance of the mRNA species in the original sample. The profile generated by such a sampling protocol is a transcriptional profile, which, as discussed above, is extremely useful for a number of approaches related to drug development.

In the practice of cyclic nucleic acid amplification, the experimentally defined parameter "$C_t$" refers to the cycle number at which the signal generated from a quantitative amplification reaction first rises above a "threshold", i.e., where there is the first reliable detection of amplification of a target nucleic acid sequence. "Reliable" means that the signal reflects a detectable level of amplified product during amplification. $C_t$ generally correlates with starting quantity of an unknown amount of a target nucleic acid, i.e., lower amounts of target result in later $C_t$. $C_t$ is linked to the initial copy number or concentration of starting nucleic acid by a simple mathematical equation:

$$\text{Log(copy number)} = aC_t + b,$$

where $a$ and $b$ are constants.

Therefore, by measuring $C_t$ for the fragments of the same gene sequence originating from two different samples, the original relative concentration of this gene sequence in these samples can be easily evaluated.

Sampling Methods and Devices

The method described herein facilitates the sampling of nucleic acid amplification reaction mixtures necessary for amplification profiling. Sampling may occur at any time during or after an amplification reaction. In one embodiment, an aliquot of the reaction is withdrawn or extruded from the tube or reaction vessel at the end of each PCR cycle. In another embodiment, an aliquot of the reaction is withdrawn or extruded from the tube or reaction vessel at the end of every several PCR cycle, e.g., every two cycles, every three cycles, every four cycles. In another embodiment, an aliquot of the reaction is withdrawn or extruded from the tube or reaction vessel at the end of a series of predetermined cycles. While a uniform sample interval will most often be desired, there is no requirement that sampling be performed at uniform intervals. As just one example, the sampling routine may involve sampling after every cycle for the first five cycles, and then sampling after every other cycle.

As discussed above, amplification methods that are continuous, rather than cyclic can also benefit from the sampling methods described herein. In such cases, samples can be withdrawn at given times during the amplification process, for example, every minute, every two minutes, every three minutes, etc.

Sampling or removal of an aliquot from an amplification reaction can be performed in any of several different general formats. First, an aliquot can be withdrawn from a reaction vessel (test tube, capillary or well in a multiwell plate) by reaching into the vessel with a pipetting device or capillary tube, preferably using an automated device. The method of sampling used for this approach will preferably be adapted to minimize contamination of the cycling reaction(s), by, for example, using pipetting tips or needles that are either disposed of after a single aliquot is withdrawn, or by incorporating one or more steps of washing the needle or tip after each aliquot is withdrawn.

Alternatively, the sampling can be done by a device which can contact a capillary to be used for capillary electrophoresis directly with the amplification reaction in order to load an aliquot into the capillary.

As another alternative, the sampling can be done using a device which includes a fluidic line (e.g. a tube) connected to a controllable valve which will open at particular cycle. Sampling devices known in the art include, for example, the multipurpose Robbins Scientific Hydra 96 pipettor, which is adapted to sampling to or from 96 well plates. This device and others like it can be readily adapted for use according to the methods of the invention.

In one embodiment, the sampling and detection are performed concurrently, such that a curve representing product abundance as a function of amplification time, e.g., measure by minutes or by PCR cycles, is generated during or soon after the amplification regimen.

For this and other aspects of the invention, it is preferred, although not necessary that the cycling be performed in a microtiter or multiwell plate format. This format, which uses plates comprising multiple reaction wells, not only increases the throughput of the assay process, but is also well adapted for automated sampling steps due to the modular nature of the plates and the uniform grid layout of the wells on the plates. Common microtiter plate designs useful according to the invention have, for example 12, 24, 48, 96, 384 or more wells, although any number of wells that physically fit on the plate and accommodate the desired reaction volume (usually 10-100 µl) can be used according to the invention. Generally, the 96 or 384 well plate format is preferred.

An automated sampling process can be readily executed as a programmed routine and avoids both human error in sampling (i.e., error in aliquot size and tracking of sample identity) and the possibility of contamination from the person sampling. Robotic samplers capable of withdrawing aliquots from thermal cyclers are available in the art. For example, the Mitsubishi RV-E2 Robotic Arm can be used in conjunction with a SciClone™ Liquid Handler or a Robbins Scientific Hydra 96 pipettor.

The robotic sampler in the embodiments described herein can be integrated with the thermal cycler, or the sampler and cycler can be modular in design. When the cycler and sampler are integrated, thermal cycling and sampling occur in the same location, with samples being withdrawn at programmed intervals by a robotic sampler. When the cycler and sampler are modular in design, the cycler and sampler are separate modules. In one embodiment, the assay plate or other container is physically moved, e.g., by a robotic arm, from the cycler to the sampler and back to the cycler.

The volume of an aliquot removed at the sampling step can vary, depending, for example, upon the total volume of the amplification reaction, the sensitivity of product detection, and the type of separation used. Amplification volumes can vary from several microliters to several hundred microliters (e.g., 5 µl, 10 µl, 20 µl, 40 µl, 60 µl, 80 µl, 100 µl, 120 µl, 150 µl, or 200 µl or more), preferably in the range of 10-150 µl, more preferably in the range of 10-100 µl. Aliquot volumes can vary from 0.1 to 30% of the reaction mixture.

In accordance with one aspect of the invention, a method is provided for quantitatively monitoring the amplification of nucleic acid sequences. In a given performance of the method, a nucleic acid amplification reaction mixture is provided. The mixture comprises a plurality of nucleic acid species. An amplification regimen is performed on the mixture, causing plural nucleic acid species to be amplified concurrently. An aliquot of the reaction mixture is dispensed at intervals preceding completion of the amplification regimen. The nucleic acid species in the aliquot are separated and detected. For respective ones of plural separated species, the quantity of those separated nucleic acid species in the aliquot is concurrently determined.

This method facilitates high throughput quantitative expression analysis on a plurality of nucleic acid species (e.g., transcripts, genes)—numerous (dozens, hundreds, thousands, etc.) in certain illustrated embodiments.

The amplification regimen may be performed on plural independent nucleic acid amplification mixtures. The plural independent amplification mixtures may be present on a multi-well container. In the illustrated embodiments, the amplification regimen comprises thermal cycling, e.g., PCR.

The dispensing may be performed following one or more cycles in the amplification regimen. For example, the dispensing may be performed following each cycle in the amplification regimen. The separating may be performed by capillary electrophoresis. In the illustrated embodiment, the plural separated species are amplified from RNA transcripts of a plurality of genes.

In one aspect, a dispensing apparatus described herein can be used in a method of monitoring the amplification of a nucleic acid sequence, preferably a plurality of sequences. In such a method, aliquots dispensed during a nucleic acid amplification regimen (e.g., after one or more cycles, preferably up to and including after each cycle) by such a dispensing apparatus are loaded into a separation apparatus, preferably into capillaries for capillary electrophoresis. The nucleic acids in the loaded samples are separated, e.g., by size and/or charge, and the separated species are detected, thereby generating an amplification profile. When the amplified nucleic acids represent transcribed RNAs, e.g., when expressed RNA is reverse-transcribed and then amplified, the amplification profile provides a transcriptional profile for the original sample. Whereas the non-linearity of amplification at late stages of the amplification process normally precludes the ability to accurately quantitate the amount of a given transcript in a nucleic acid sample by measuring amplicon abundance after multiple cycles, the transcriptional profile generated in this manner provides quantitative as well as qualitative data that do permit such determination. The detection of amplicon abundance at various cycles during the amplification provides a real time representation of how the amplification proceeded for each species amplified and detected in a given reaction. Because non-linearity in the amplification process can be accounted for in such a real time profile, the profile permits the efficient quantitative determination of the amount of RNA corresponding to a given amplicon in an original sample. This is but one example of the advantages provided by a real time transcriptional profile generated by such a method.

Other advantages provided by the real time profiling performed in such a manner include, for example, the ability to follow the amplification profiles for multiple amplicons, representing, for example, multiple transcripts in a single sample. Because the size separation by, for example, CE, can resolve species differing by as little as one nucleotide, the sample withdrawn from an amplification reaction can have multiple differently sized amplicons, each representing a different transcript in the original sample. When this is considered along with the simultaneous amplification of multiple samples, as in amplification performed in multi-well plates or in parallel in multiple tubes or capillaries, the amount of information obtainable increases dramatically.

The sampling and analysis methods described herein are particularly well suited for the comparative analysis of gene expression. That is, the methods described permit one to generate a transcriptional profile for a given cell or tissue and to compare that profile with the profile from another cell or tissue to determine differences in the gene expression patterns. Such differences are useful for diagnostic purposes where, for example, a given pattern of expression is elaborated in a particular disease condition. In that instance, one would compare transcriptional profiles of a sample from an individual suspected of having a particular disease condition with the transcriptional profile from one or more individuals known to have that disease condition. Similarities between the patterns of expression would confirm the diagnosis.

Comparative analysis of transcriptional profiles is also useful for the identification and/or validation of genes involved in disease. This approach is similar to the use of microarray hybridization methods, but has the added power provided by the ability to obtain quantitative data. In this approach, samples from healthy and diseased individuals are used to generate transcriptional profiles of multiple transcripts. The profiles can be generated using primers that hybridize to known genes, or, alternatively, can be generated using random or, preferably, semi-random primers. Semi-random primers are primers that have variation introduced within the 3'-terminal 1, 2 or 3 nucleotides. In one aspect, one can use a set of reverse-transcription primers with variation introduced at the 3' terminal 1, 2 or 3 nucleotides (primers of this design are used in the art for the method of "differential display," described by Liang & Pardee (1998, Mol. Biotechnol. 10:261-7)). A further aspect of this primer design involves the addition of an invariant tag sequence 5' of the variable region. Amplification can then be preformed using one or more arbitrary upstream amplification primers (generally about 10-14 nucleotides, but can be longer) with a downstream amplification primer that hybridizes to the complement of the invariant region of the reverse transcription primer. One or more of the primers can be labeled, for example, with one or more fluorophores. In this manner, a set of transcripts is amplified; when combined with the sampling approach described herein, the amplification generates a transcriptional profile for a subset of the transcripts present in the original sample. This profile can then be compared to those of other samples produced with the same combination of primers.

Differences in the profiles obtained from different samples amplified using the same set of reverse-transcription and amplification primers can be used for diagnostic or prognostic purposes, for predicting the response of an individual to a drug, and for drug target identification and drug screening. The differences observed between samples from healthy and diseased individuals can be indicative of genes related to the disease state. Differences observed between samples from cells treated with or without a drug or other influence can be used to screen for drug effects on a target gene, or for example, on the pattern of genes expressed in a given disease state. Additional applications for the transcriptional profiles permitted by the sampling methods described herein will be apparent to the skilled artisan.

Differences in the overall pattern of expression, for example, transcripts present in one sample but not in another, as well as quantitative differences in expression of individual transcripts from one sample to the next are determined in the manner described above. Whereas classical differential display is notoriously error-prone when one observes differences in abundance of an amplicon, rather than the discrete presence or absence of the amplicon (primarily because detection occurs only after multiple amplification cycles), the sampling method described herein permits meaningful distinctions based on differences in amplicon abundance.

In the transcriptional profiling approach using arbitrary or randomized primers, the identity of the amplified transcripts will generally not be known. However, amplified products that vary in representation between one sample and another can, if desired, be isolated and sequenced to identify the transcript (the isolated sequence can be used as a probe to isolate the full length transcript sequence using methods well known in the art).

To summarize, the transcriptional profiles generated using the sampling methods described herein can represent the transcriptional profile of individual known transcription units or genes, multiple known transcription units or genes, or multiple unknown transcription units or genes.

It is preferred that sample or aliquot dispensing is performed by an automated apparatus. "Automated" can refer to an apparatus that follows a programmed routine from start to finish without user input during the process, an apparatus that requires user input for each repetition of dispensing, or any combination thereof. Preferably the apparatus does not require user input after the initiation of a dispensing routine.

FIG. 1 is a block diagram of a system for amplification profiling. An RNA/DNA amplification apparatus 12 is provided to produce amplified product of nucleic acid molecules (RNA or DNA). Amplification apparatus 12 comprises a reaction system, described more fully hereinbelow, to cause amplification of nucleic acids in the reaction mixture of respective ones of plural samples held by a solution holder 13.

An aliquot dispensing apparatus 14 is coupled to amplification apparatus 12, and dispenses, from each sample of a set of plural samples held by solution holder 13, plural aliquots of a given sample to respective aliquot holders in an aliquot holding structure 16. Aliquot holding structure 16 may comprise one of a set of microtitre trays.

A separation and quantitative analysis system 20 is provided which is coupled to a data processing system for allowing processing, display, and/or storage of data produced by system 20.

A process control mechanism 18, e.g., a microprocessor, is coupled to apparatuses 12, 14, and 20 to control operation of the same. Process control mechanism may be programmed to control each action performed by these apparatuses without human intervention. Optionally, the program may allow for any desired degree of human intervention. For example, process control mechanism 18 may be provided with a computer interface (not shown) that allows a user to make adjustments to the amplification and dispensing processes performed by apparatuses 12 and 14 (and optionally also to the separation and quantitative analysis performed by system 20) by either changing the program altogether or by influencing the process by interjecting additional acts or modifications to acts to be performed by such apparatuses.

In the illustrated embodiment, aliquot dispensing apparatus 14 and process control mechanism 18 collectively operate to automatically dispense, from each sample of a set of plural samples held by solution holder 13, plural aliquots of a given sample to respective separate aliquot holders in aliquot holding structure 16. More specifically, the plural aliquots are dispensed at respective different times during an amplification regimen. Accordingly, aliquot dispensing apparatus is provided with one or more automated actuation mechanisms 15 (e.g., computer actuable arms, robotic arms), and process control mechanism comprises a dispense control process object 19 for controlling the operation of such automated actuation mechanisms 15.

The illustrated amplification apparatus 12 may perform an amplification regimen that is cyclic or that is non-cyclic, or continuous. Moreover, the apparatus may perform a thermal amplification regimen (e.g., PCR), or it may perform an amplification regimen not involving a thermal approach (e.g., ligase chain reaction (LCR)). More information is provided hereinbelow regarding approaches for amplification.

Separation and quantitative analysis system 20 may comprise any suitable device or system that analyzes plural samples and separates, from respective ones of the samples (aliquots, in the illustrated embodiment) individual nucleic acid molecules based on physical properties of the molecules (e.g., charge, length, mass). By way of example, system 20 may comprise a CE (capillary electrophoresis) device, a liquid chromatography mass spectrometry (LC-MS) apparatus, or a high performance liquid chromatography (HPLC) apparatus.

Figure 2:
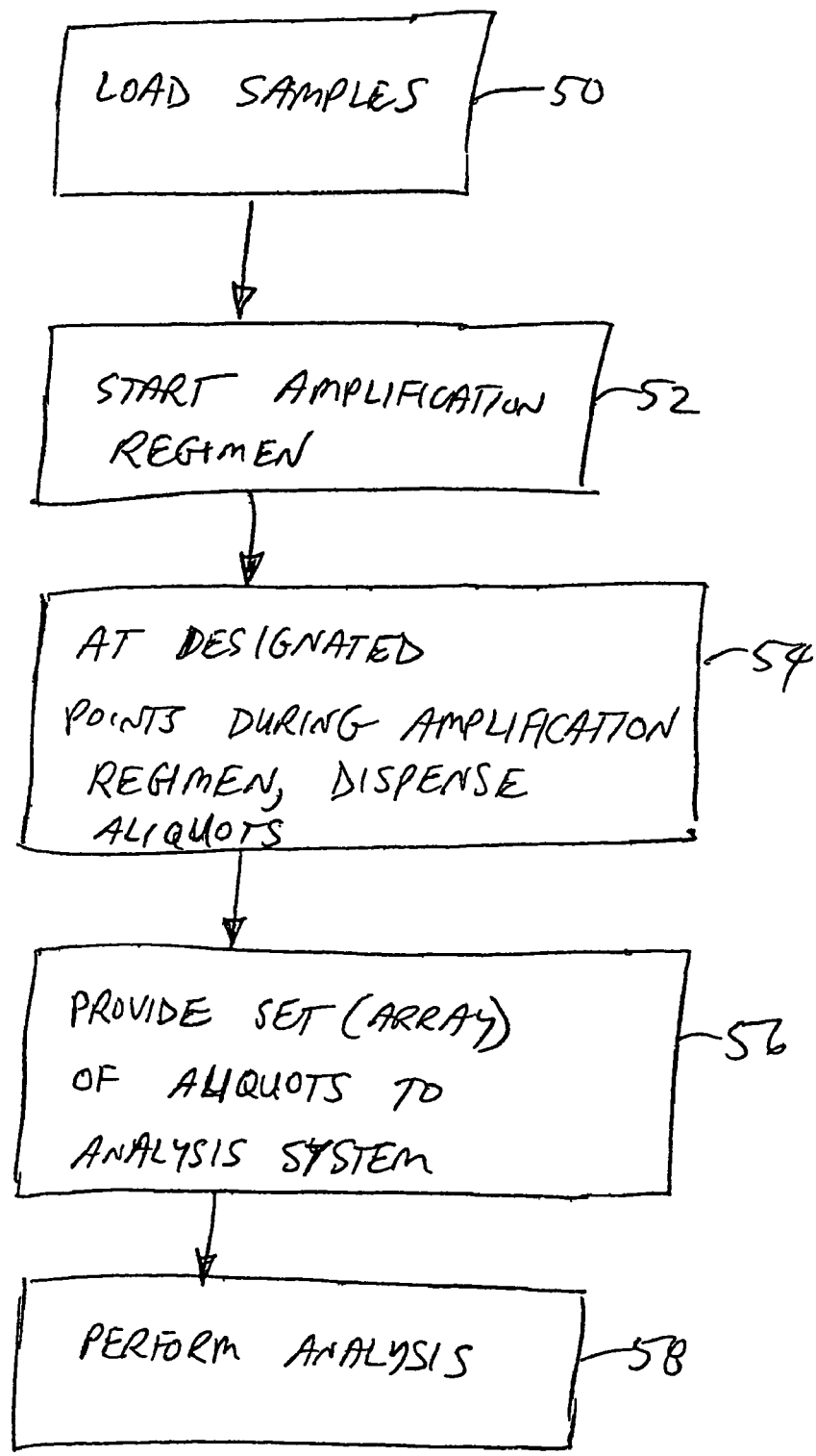
FIG. 2 is a flow chart of a process for performing amplification profiling.

FIG. 2 is a flow chart of a process for performing amplification profiling using the apparatus shown in FIG. 1. In an initial act 50, samples are loaded into solution holder 13. In act 52, an amplification regimen is started. Then, at act 54, at designated points in time during the amplification regimen, aliquots are dispensed into respective different aliquot holders.

In act 56, a given set of aliquots, corresponding to a particular point in the amplification regimen, is provided for input to separation system 20. At act 58, the separation and quantitative analysis is performed by system 20.

Figure 3:
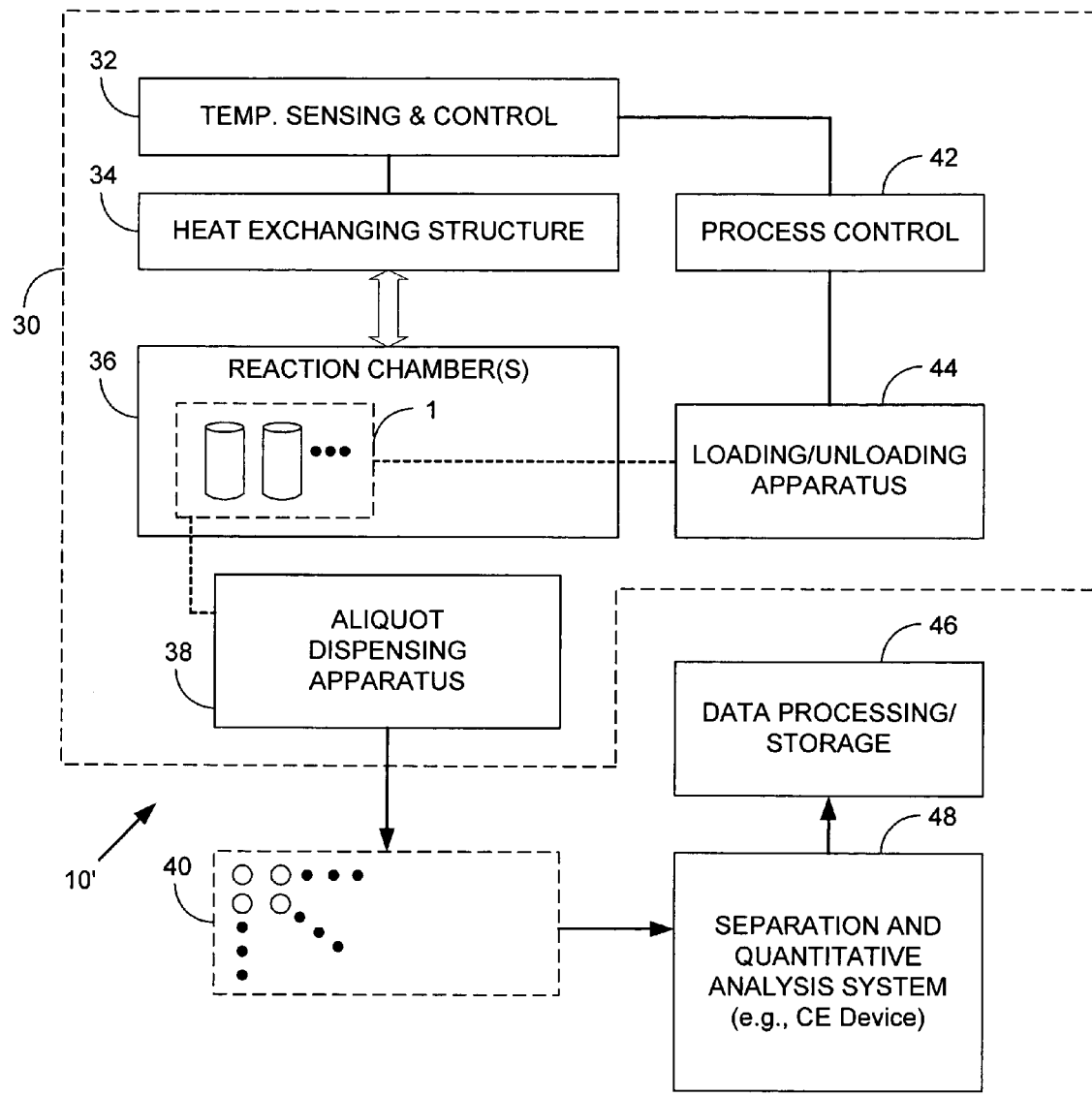
FIG. 3 is a block diagram of an amplification profiling system comprising a PCR apparatus with an aliquot dispensing apparatus.
Figure 5:
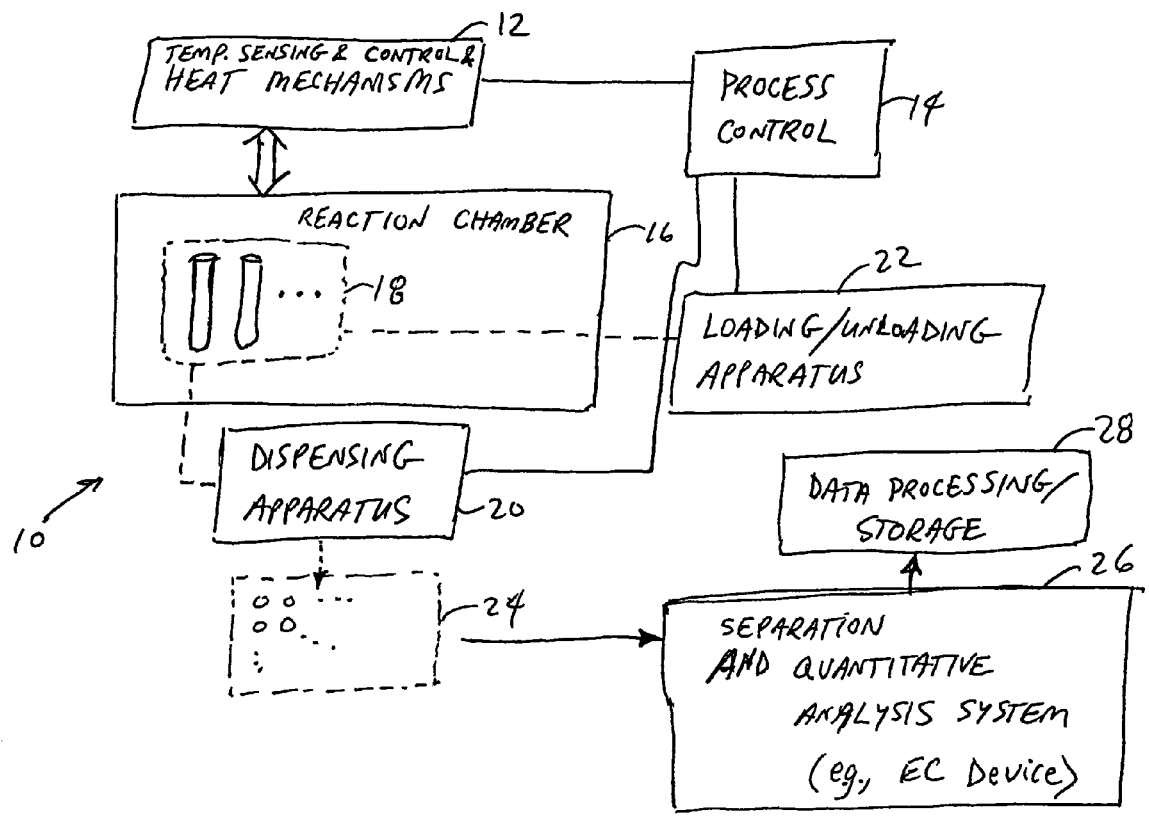
FIG. 5 is a schematic diagram of a system for concurrently quantitatively monitoring and analyzing the amplification of numerous species of nucleic acid sequences. The species may specifically be amplified from RNA transcripts of a plurality of genes. The system comprises a temperature cycling amplification machine 10—e.g., a PCR device. Mechanisms 12 are provided for temperature sensing and control and heat, and are coupled to a reaction chamber 16 which holds structure(s) 18 carrying one or more sets (e.g., arrays) of samples. The samples may be held, e.g., by wells, tubes, or capillaries.

FIG. 3 is a schematic diagram of an amplification profiling system—for concurrently quantitatively monitoring and analyzing the amplification of numerous species of nucleic acid sequences. The species may specifically be amplified from RNA transcripts of a plurality of genes. The system comprises a thermal cycling amplification machine—e.g., a PCR apparatus 30. Mechanisms 32 are provided for temperature sensing and control. A heat exchanging structure 34 is provided, which is coupled to one or more reaction chambers 36 which holds one or more structures 35 carrying one or more sets (e.g., arrays) of samples. The samples may be held, e.g., by wells, tubes, or capillaries.

An aliquot dispensing apparatus 38 is provided which is controllable to automatically, on demand from a process control 42, dispense aliquots from the samples in structure(s) 35. Dispensing apparatus 38 may comprise any mechanisms known in the art or commercially available for automatically acquiring aliquots from respective samples and placing such aliquots into an aliquot holding structure 40. Process control 42 may comprise, e.g., a computer and a computer user interface allowing a human operator to intercede in the process or program the process. Loading/unloading apparatus 44 is provided for loading and unloading the samples for a given amplification regimen.

In the illustrated embodiment, aliquot dispensing apparatus is provided with one or more automated actuation mechanisms 39 (e.g., computer actuable arms, robotic arms), and process control mechanism 42 comprises a dispense control process object 43 for controlling the operation of such automated actuation mechanisms 39.

Analysis system 48, which may comprise a CE device, receives a set of aliquots from structure(s) 40. Aliquot structure(s) 40 may be made compatible with the analysis system 48 to facilitate an easy interface and input into the analysis system.

Data processing/storage system 46 stores and allows processing of data produced by analysis system 48.

Various components of the illustrated thermal amplification apparatus 30 may comprise mechanisms known in the art or available in off-the-shelf devices, e.g., PCR devices. By way of example, but not for purposes of limitation, device 30 (or one or more parts thereof) may be made in accordance with one or more of U.S. Pat. Nos. 5,038,852 and 5,827,480.

The illustrated analysis system may comprise mechanisms known in the art or available in off-the-shelf devices, e.g., CE devices. By way of example, but not for purposes of limitation, device 26 (or one or more parts thereof) may be made in accordance with one or more of U.S. Pat. Nos. 6,217,731 and 6,001,230.

In operation, samples are loaded into the reaction chamber(s) 36. An amplification regimen is started. At designated points during the amplification regimen, the aliquots are dispensed (automatically, in the illustrated embodiment) for subsequent analysis by analysis system. The aliquots are provided to the analysis system. Such dispensed samples may be analyzed right away or they may be set aside for batch processing once all the sets of intermediate (mid-amplification regimen) aliquots are obtained and after the regimen is complete. The samples are then analyzed.

PCR may be performed with automatic sampling (by dispensing apparatus 20) after each PCR cycle, after each set of cycles, or at given points as defined by a user during the PCR amplification regimen yet before completion of the regimen. The resulting aliquots may be dispensed into a sample tray. The sample trays may be stacked (e.g., manually) and analyzed by an analysis system (e.g., a CE device).

Apparatus 30 dispenses in a sample collecting tray (or plate) an aliquot of the reaction mixture after each amplification (temperature) cycle or after a predetermined number of such cycles. The aliquot dispensing apparatus 38 may comprise an automatically controllable mechanism for withdrawing an aliquot from the reaction mixture by pipetting (e.g., autosampling) or by applying pressure to one end of the reaction vessel (where the samples are carried by a capillary, tube, or other kind of vessel which has an inlet and outlet for liquid movement).

Amplification Methods

Any nucleic acid amplification method can benefit from an automated sampling method as described herein. Of particular interest are amplification methods that involve repeated cycles of nucleic acid synthesis or polymerization, a number of which are known to those skilled in the art.

The most commonly used amplification method is thermal cycling PCR, originally described by Mullis and Faloona (1987, Meth. Enzymol. 155:335-350). In thermal cycling PCR, two oligonucleotide primers, a template and a thermostable nucleic acid polymerase are generally used for each template sequence to be amplified. In the general PCR scheme, one of the oligonucleotide primers anneals to a template nucleic acid strand. The annealed primer is extended by the thermostable template-dependent nucleic acid polymerase, and that polymerization product has a sequence complementary to the second primer such that the polymerization product can serve as template for the extension of the second primer. The polymerization product is thermally denatured to separate the strands, and the pair of primers is annealed to the respective strands and extended. Because each extension product serves as the template for subsequent extension reactions, the target sequence is exponentially amplified.

Numerous variations on the general principle of thermal cycling PCR have been described and are known to those of skill in the art. When amplification profiling is to be performed, e.g., in order to derive quantitative information regarding the abundance of template in a biological sample, sampling can be performed after various cycles in the process. Ideally, an aliquot is withdrawn or extruded from the amplification reaction mixture after each cycle in the amplification regimen. Sampling can be performed after any desired cycles, e.g., after every other cycle, every third cycle, every fourth cycle, etc., but the most detailed and accurate information regarding the amplification profile will be obtained when sampling is performed after each cycle in the regimen. This is particularly so when more than one target amplification product is monitored in a single amplification reaction or set of amplification reactions. This is so because the kinetics of amplification of different target sequences can differ dramatically with the sequence and initial abundance of the different target sequences. Sampling at every cycle will permit the generation of a complete amplification profile for each target in a single reaction mixture regardless of the kinetics of amplification for the individual targets.

Another method of nucleic acid amplification that can benefit from the sampling methods described herein is isothermal, Self-Sustained Sequence Replication (3SR; Gingeras et al., 1990, Annales de Biologie Clinique, 48(7): 498-501; Guatelli et al., 1990, Proc. Natl. Acad. Sci. U.S.A., 87: 1874). The contents of these articles are herein incorporated by reference. 3SR is an outgrowth of the transcription-based amplification system (TAS), which capitalizes on the high promoter sequence specificity and reiterative properties of bacteriophage DNA-dependent RNA polymerases to decrease the number of amplification cycles necessary to achieve high amplification levels (Kwoh et al., 1989, Proc. Natl. Acad. Sci. U.S.A., 83: 1173-1177).

In 3SR, each priming oligonucleotide contains a bacteriophage RNA polymerase binding sequence and the preferred transcriptional initiation sequence, e.g., the T7 RNA polymerase binding sequence (TAATACGACTCACTATA [SEQ ID NO: 1]) and the preferred T7 polymerase transcriptional initiation site. The remaining sequence of each primer is complementary to the target sequence on the molecule to be amplified.

Exemplary 3SR conditions are described herein as follows. The 3SR amplification reaction is carried out in 100 µl and contains the target RNA, 40 mM Tris-HCl, ph 8.1, 20 mM MgCl2, 2 mM spermidine-HCl, 5 mM dithiothreitol, 80 µg/ml BSA, 1 mM dATP, 1 mM dGTP, 1 mM dTTP, 4 mMATP, 4 mM CTP, 1 mM GTP, 4 mM dTTP, 4 mM ATP, 4 mM CTP, 4 mM GTP, 4 mMUTP, and a suitable amount of oligonucleotide primer (250 ng of a 57-mer; this amount is scaled up or down, proportionally, depending upon the length of the primer sequence). Three to six attomoles of the nucleic acid target for the 3SR reactions is used. As a control for background, a 3SR reaction without any target is run in parallel. The reaction mixture is heated to 100° C. for 1 minute, and then rapidly chilled to 42° C. After 1 minute, 10 units (usually in a volume of approximately 2 µl) of reverse transcriptase, (e.g. avian myoblastosis virus reverse transcriptase, AMV-RT; Life Technologies/Gibco-BRL) is added. The reaction is incubated for 10 minutes, at 42° C. and then heated to 100° C. for 1 minute. (If a 3SR reaction is performed using a single-stranded template, the reaction mixture is heated instead to 65° C. for 1 minute.) Reactions are then cooled to 37° C. for 2 minutes prior to the addition of 4.6 µl of a 3SR enzyme mix, which contains 1.6 µl of AMV-RT at 18.5 units/µl, 1.0 µl T7 RNA polymerase (both e.g. from Stratagene; La Jolla, Calif.) at 100 units/µl, and 2.0 µl E. Coli RNase H at 4 units/el (e.g. from Gibco/Life Technologies; Gaithersburg, Md.). It is well within the knowledge of one of skill in the art to adjust enzyme volumes as needed to account for variations in the specific activities of enzymes drawn from different production lots or supplied by different manufacturers. Variations can also be made to the units of the enzymes as necessary. The reaction is incubated at 37° C. for 1 hour and stopped by freezing.

Sampling can be performed at any stage of the 3SR reaction. Because 3SR proceeds continuously at a single temperature, there are not individual cycles at which aliquots will be withdrawn. In this instance, sampling can be performed at set times during the amplification incubation period, for example, every minute, every two minutes, every three minutes, etc. Nucleic acids in the aliquots withdrawn or extruded are separated and nucleic acids detected, thereby permitting the generation of an amplification profile, from which the abundance of target in the initial sample can be determined.

3SR is also referred to by some as Nucleic Acid Sequence Based Amplification, or NASBA (see for example, Compton, 1991, Nature, 350: 91-92; Kievits-et al., 1991, J. Virol Meth. 35: 273-286, each of which is incorporated herein by reference).

Another method of nucleic acid amplification that is of use according to the invention is the DNA ligase amplification reaction (LAR), which has been described as permitting the exponential increase of specific short sequences through the activities of any one of several bacterial DNA ligases (Wu and Wallace, 1989, Genomics, 4: 560; Barany, 1991, Proc. Natl. Acad. Sci. USA 88: 189, each of which is incorporated herein by reference). This technique is based upon the ligation of oligonucleotide probes. The probes are designed to exactly match two adjacent sequences of a specific target nucleic acid. The amplification reaction is repeated in three steps in the presence of excess probe: (1) heat denaturation of double-stranded nucleic acid, (2) annealing of probes to target nucleic acid, and (3) joining of the probes by thermostable DNA ligase. The reaction is generally repeated for 20-30 cycles. The sampling methods disclosed herein permit the generation of a detailed amplification profile. As with any cyclic amplification protocol, sampling can be performed after any cycle, but preferably after each cycle.

Rolling circle amplification (RCA) is an alternative amplification technology that may prove to have as large an impact as PCR. This technique draws on the DNA replication mechanism of some viruses. In RCA, similar to the replication technique used by many viruses, a polymerase enzyme reads off of a single promoter around a circle of DNA—continuously rolling out linear, concatenated copies of the circle. In such linear RCA, the reaction can run for three days, producing millions of copies of the small circle sequence. An exponential variant has been developed in which a second promoter displaces the double strands at each repeat and initiates hyperbranching in the DNA replication, creating as many as $10^{12}$ copies per hour.

Another amplification method that can benefit from the sampling methods disclosed herein is strand-displacement amplification (SDA; Walker et al., 1992, Nucleic Acids Res., 20: 1691-1696; Spargo et al., 1993, Mol. Cellular Probes 7: 395-404, each of which is incorporated herein by reference). SDA uses two types of primers and two enzymes (DNA polymerase and a restriction endonuclease) to exponentially produce single-stranded amplicons asynchronously. A variant of the basic method in which sets of the amplification primers were anchored to distinct zones on a chip reduces primer-primer interactions. This so-called "anchored SDA" approach permits multiplex DNA or RNA amplification without decreasing amplification efficiency (Westin et al., 2000, Nature Biotechnology 18: 199-204, incorporated herein by reference). SDA can benefit from the sampling methods disclosed herein, as they permit the generation of a detailed amplification profile.

One of the limitations of thermal cycled PCR and, for that matter, any method that requires a specific primer for each different target sequence in a reaction is that the concentration of primers tends to introduce artifacts to the reactions. Primer-primer interactions often result in the incorporation of primers into complexes independent of template. A common example is the so-called "primer-dimer" encountered in thermal cycling PCR. When the 3' end of one primer hybridizes to a site within another primer, the polymerase enzyme can extend the primer to generate a template-independent product. Because the concentration of amplification primers is generally in excess of specific target sequences, a large number of primer dimer artifacts can be generated when there is the necessary complementarity between two or more primers. It follows that the higher the number of different primers in an amplification reaction, the greater the chance that one will find a region of complementarity in another and result in primer dimer-type artifacts. As one attempts to multiplex additional target sequence amplifications into a single reaction mixture, the chances for this type of artifact increase dramatically.

Sampling methods as disclosed herein can help in avoiding or at least minimizing the effects of artifacts induced by the presence of multiple primers. First, when sampling is used, the nucleic acid products in the samples can be separated by size and detected, and primer dimer-type artifacts can be excluded by their small size. Another approach is to limit the number of different primers in the amplification reaction. One approach to this is described in U.S. patent application No. 60/372,045, which is incorporated herein by reference. The application describes a number of approaches that permit the detection of multiple different amplification products in a single reaction mixture. Several of those methods reduce the number of different primers necessary for quantitative multiplex PCR by incorporating downstream primers comprising a common tag sequence into each of a number of different reverse-transcription products. The first round of amplification additionally incorporates one or more upstream primers comprising a different common tag sequence. Subsequent amplification is then performed with a single pair of amplification primers that recognize the common tag sequences. The sizes of the various amplicons is selected such that subsequent separation of the products can distinguish the various species amplified in the reaction. This approach has the benefit that a smaller number of primers is present in the amplification reaction. An additional benefit is that differences in the annealing efficiency for the primers are minimized by the reduction in the number of different amplification primers used. Differences in primer annealing efficiency, caused by, for example, different G+C content of the primers, is known to influence the reliability of multiplex quantitative amplification approaches.

FIG. 4 shows a schematic diagram of an amplification approach wherein two different targets of different size are amplified with a single pair of amplification primers that anneal to common tag sequences incorporated by primer extension. T1 is a downstream tag sequence common to all amplicons, and T2 is an upstream tag sequence common to all amplicons (T1' and T2' denote their respective complements). The tag sequences are incorporated as part of the sequence of primer extension primers that are annealed to the target sequence and extended. Each primer extension primer has a region complementary to a sequence on the target sequence or the complement of the target sequence (designated a, b, c and d and a', b', c' and d' in the figure), and a tag sequence. Two rounds of primer extension primer annealing and extension generates a set of molecules each comprising both an upstream and a downstream tag sequence or its complement. At this point, primer extension primers are removed and amplification is performed using amplification primers corresponding to the tag sequences T1 and T2, one of which primers is fluorescently labeled. Subsequent size separation, (e.g., by capillary electrophoresis) and detection distinguishes the targets by size and determines the abundance of the individual targets. In this way, two different target sequences are amplified with a single pair of amplification primers. This approach can be scaled up to include numerous differently-sized target sequences that are then resolved by size and detected. Further multiplexing can occur without dramatically increasing the number of amplification primers by using a set of optically distinguishable fluorescent labels on additional amplification primers.

Amplification Reaction Devices

Devices for performing the amplification reactions must be capable of achieving and maintaining reaction temperatures required for the amplification reaction in one or more tubes, capillaries or multiwell containers. Any device capable of achieving and maintaining the temperature or temperatures necessary for an amplification reaction can be used. As a non-limiting example, convenient devices include thermal cyclers commonly used for PCR amplification. Thermal cyclers are widely available commercially.

Amplification reaction devices such as thermal cyclers can be interfaced with a sampling device, for example, in a modular design, or the sampling device can be integral with the amplification reaction device. In one aspect, the amplification reactions themselves are performed in capillary or other tubes that are open at one or both ends, and sampling is performed by applying pressure or a (vacuum) to one end of the tube such that a portion of the reaction mixture is extruded from the tube and collected by a sampling device. Thermal cyclers capable of accepting tubes, including capillary tubes, are commercially available and include, for example the Lightcycler™ (Roche Molecular Biochemicals, Indianapolis, Ind.), the RapidCycler™ (Idaho Technology, Salt Lake City, Utah) and the BioOven III Thermocycler (St. John Associates, Beltsville, Md.).

Separation and Detection Methods

Any of a number of different nucleic acid separation methods can be used in the methods disclosed herein. For example, various adaptations of electrophoresis and liquid chromatography are well suited for separating nucleic acid species in a sample from an amplification reaction.

Electrophoretic separation is preferably performed as capillary electrophoresis (CE), due to the small sample sizes necessary and the speed and resolution achievable. Another benefit of CE is that there exist a variety of off-the-shelf CE devices that are interfaced with fluorescence detectors, for example, high throughput CE equipment is available commercially, for example, the HTS9610 High Throughput Analysis System and SCE 9610 fully automated 96-capillary electrophoresis genetic analysis system from Spectrumedix Corporation (State College, Pa.). Others include the P/ACE 5000 series from Beckman Instruments Inc (Fullerton, Calif.) and the ABI PRISM 3100 genetic analyzer (Applied Biosystems, Foster City, Calif.). Each of these devices comprises a fluorescence detector that monitors the emission of light by molecules in the sample near the end of the CE column. The standard fluorescence detectors can distinguish numerous different wavelengths of fluorescence emission, providing the ability to detect multiple fluorescently labeled species in a single CE run from an amplification sample.

CE devices capable of running 96 samples at a time mesh nicely with, for example, thermal cyclers or other amplification devices that run multiple samples simultaneously. CE devices that provide automated sample loadiFng, electrophoresis and detection for multiple samples in parallel are described in U.S. Pat. Nos. 6,217,731 and 6,001,230. As an alternative to fluorescence detection, a CE device can be interfaced with a mass spectrometry device for detection of the various nucleic acid species in an amplification reaction by molecular mass (CE/MS). Mass spectrometry devices capable of such detection are commercially available.

Liquid chromatography (LC) is another option for the separation of nucleic acids in samples withdrawn or extruded from an amplification reaction. Commonly, LC is coupled with mass spectrometry (LC/MS), such that the mass of HPLC-separated species is determined by mass spectrometry. LC/MS systems are commercially available, for example, from Agilent Technologies (e.g., the 1100 Series™ LC/MS) and from Applied Biosystems (e.g., the API 3000™ or API 4000™ LC/MS systems), among others.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of analyzing a nucleic acid amplification comprising:
   providing a nucleic acid amplification reaction mixture comprising a plurality of different amplification templates;
   subjecting said reaction mixture to an amplification regimen;
   dispensing or withdrawing an aliquot from said reaction mixture at plural stages during said amplification regimen;
   separating and detecting nucleic acids in said aliquot, wherein said separating comprises capillary electrophoresis;
   determining the quantity of a plurality of separated nucleic acid species in said aliquot, wherein said plurality of different amplification templates comprises at least five different amplification templates and
   for each said separated nucleic acid species from each said stage, correlating the quantity of said species with the stage at which said aliquot comprising said species was dispensed, wherein said correlating generates an amplification profile of said nucleic acid amplification, and wherein said amplification profile provides quantitative information regarding the abundance of said plurality of different amplification templates in said amplification reaction mixture at the start of said amplification regimen.

2. The method of claim 1 wherein said plurality of different amplification templates comprises at least ten different amplification templates.

3. The method of claim 1 wherein said plurality of different amplification templates comprises at least 20 different amplification templates.

4. The method of claim 1 wherein said plurality of different amplification templates comprises at least 50 different amplification templates.

5. The method of claim 1 wherein said plurality of different amplification templates comprises at least 100 different amplification templates.

6. The method of claim 1 wherein said plurality of different amplification templates comprises at least 200 different amplification templates.

7. The method of claim 1 wherein a plurality of amplification reaction mixtures is subjected to said method.

8. The method of claim 7 wherein said plurality of amplification reaction mixtures is subjected to said method simultaneously.

9. The method of claim 1 wherein said method generates an amplification profile for a plurality of amplified nucleic acid species.

10. The method of claim 1 wherein said amplification profile is a transcriptional profile.

11. The method of claim 1 wherein said nucleic acid amplification regimen comprises thermal cycling.

12. The method of claim 1 wherein said nucleic acid amplification regimen comprises isothermal cycling.

13. The method of claim 1 wherein said nucleic acid amplification regimen comprises PCR.

14. The method of claim 1 wherein said nucleic acid amplification regimen comprises a method selected from the group consisting of ligase-mediated amplification, NASBA, and rolling circle amplification.

15. The method of claim 1 wherein said aliquot is dispensed into a receptacle having a plurality of aliquot-receiving sites.

16. The method of claim 15 wherein said receptacle is a multiwell plate.

17. The method of claim 1 wherein said aliquot is dispensed into or onto a receptacle capable of holding a plurality of aliquots without mixing among said aliquots.

18. The method of claim 15 wherein said receptacle comprises a plurality of CE capillaries.

19. The method of claim 1 wherein said amplification regimen is cyclic.

20. The method of claim 19 wherein said dispensing or withdrawing is performed after each of a plurality of cycles.

21. The method of claim 19 wherein said dispensing or withdrawing is performed after every cycle in said regimen.

22. The method of claim 15 wherein said detecting comprises detection of one or more fluorescent labels.

23. The method of claim 15 wherein said detecting comprises mass spectrometry.

24. The method of claim 1 wherein said amplification regimen is performed in a container, and wherein said aliquot dispensing is performed by withdrawing said aliquot from said container.

25. The method of claim 16 wherein said container is a well or a test tube.

26. The method of claim 1 wherein said amplification regimen is performed in a container, and wherein said dispensing is performed by extruding said aliquot from said container.

27. The method of claim 26 wherein said amplification regimen is performed in a container open at one or both ends.

28. The method of claim 26 wherein said container is a capillary tube.

29. A method of analyzing the expression of a plurality of RNA transcripts between first and second gene expressing entities, said method comprising
   providing a first nucleic acid amplification reaction mixture, said mixture comprising a plurality of different amplification templates, wherein said amplification templates comprise reverse transcription products from a plurality of RNA transcripts from a first gene expressing entity;

providing a second nucleic acid amplification reaction mixture, said mixture comprising a plurality of different amplification templates, wherein said amplification templates comprise reverse transcription products from a plurality of RNA transcripts from a second gene expressing entity;

subjecting said reaction mixtures to an amplification regimen;

dispensing or withdrawing an aliquot from said first and said second reaction mixtures at plural stages during said amplification regimen;

separating and detecting nucleic acids in said aliquot, wherein said separating comprises capillary electrophoresis;

determining the quantity of a plurality of separated nucleic acid species in said aliquot, wherein said plurality of RNA transcripts comprises at least five different RNA transcripts for each said separated nucleic acid species from each said stage, correlating the quantity of said species with the stage at which said aliquot comprising said species was dispensed, thereby generating a transcriptional profile of said plurality of RNA transcripts expressed by said first and said second gene expressing entities; and comparing said transcriptional profile from said first gene expressing entity with said transcriptional profile from said second gene expressing entity, wherein said comparing provides quantitative information regarding the abundance of said plurality of different amplification templates produced by said first and second entities.

30. The method of claim 29 wherein said plurality of RNA transcripts comprises at least ten different RNA transcripts.

31. The method of claim 29 wherein said plurality of RNA transcripts comprises at least 20 different RNA transcripts.

32. The method of claim 29 wherein said plurality of RNA transcripts comprises at least 50 different RNA transcripts.

33. The method of claim 29 wherein said plurality of RNA transcripts comprises at least 100 different RNA transcripts.

34. The method of claim 29 wherein said plurality of RNA transcripts comprises at least 200 different RNA transcripts.

35. The method of claim 29 wherein said amplification regimen is cyclic.

36. The method of claim 35 wherein said nucleic acid amplification regimen comprises thermal cycling.

37. The method of claim 35 wherein said nucleic acid amplification regimen comprises isothermal cycling.

38. The method of claim 35 wherein said nucleic acid amplification regimen comprises PCR.

39. The method of claim 29 wherein said nucleic acid amplification regimen comprises ligase-mediated amplification, NASBA, and rolling circle amplification.

40. The method of claim 29 wherein said aliquot is dispensed into a receptacle having a plurality of aliquot-receiving sites.

41. The method of claim 40 wherein said receptacle is a multiwell plate.

42. The method of claim 40 wherein said receptacle comprises a plurality of CE capillaries.

43. The method of claim 35 wherein said dispensing or withdrawing is performed after a plurality of cycles.

44. The method of claim 35 wherein said dispensing or withdrawing is performed after every cycle in said regimen.

45. The method of claim 29 wherein said detecting comprises detection of one or more fluorescent labels.

46. The method of claim 29 wherein said detecting comprises mass spectrometry.

47. The method of claim 29 wherein said amplification regimen is performed in a container, and wherein said aliquot dispensing is performed by withdrawing said sample from said container.

48. The method of claim 47 wherein said container is a well or a test tube.

49. The method of claim 43 wherein said amplification regimen is performed in a container, and wherein said dispensing is performed by extruding said aliquot from said container.

50. The method of claim 49 wherein said container is a capillary tube.

51. A method of monitoring the amplification of a nucleic acid sequence, the method comprising:

providing a nucleic acid amplification reaction mixture comprising a template of said nucleic acid sequence;

performing an amplification regimen on the mixture;

automatically dispensing an aliquot of said reaction mixture at plural stage intervals throughout the amplification regimen;

separating and detecting at least five nucleic acid species in said aliquot, wherein said separating comprises capillary electrophoresis; and, for respective ones of plural separated species, determining the quantity of separated nucleic acid in said aliquot.

52. A method of determining the transcription profile of a nucleic acid sequence, the method comprising:

providing a nucleic acid amplification reaction mixture;

performing an amplification regimen on the mixture;

dispensing an aliquot of said reaction mixture at plural stage intervals throughout the amplification regimen;

separating and detecting at least five nucleic acid species in said aliquot, wherein said separating comprises capillary electrophoresis; and, for respective ones of plural separated species, determining the quantity of separated nucleic acid in said aliquot whereby a transcription profile is determined for said nucleic acid species, and wherein said profile provides quantitative information regarding the abundance, in said amplification reaction mixture, at the start of said amplification regimen, of said at least five nucleic acid species.

53. A method of analyzing a nucleic acid amplification comprising:

providing a nucleic acid amplification reaction mixture comprising a plurality of different amplification templates;

subjecting said reaction mixture to a PCR amplification regimen;

dispensing or withdrawing an aliquot from said reaction mixture at plural stages during said amplification regimen;

separating and detecting nucleic acids in said aliquot, wherein said separating comprises capillary electrophoresis;

determining the quantity of a plurality of separated nucleic acid species in said aliquot, and for each said separated nucleic acid species from each said stage, correlating the quantity of said species with the stage at which said aliquot comprising said species was dispensed, wherein said correlating generates an amplification profile of said nucleic acid amplification, and wherein said amplification profile provides quantitative information regarding the abundance of said plurality of different amplification templates in said amplification reaction mixture at the start of said amplification regimen.

54. A method of analyzing the expression of a plurality of RNA transcripts between first and second gene expressing entities, said method comprising
providing a first nucleic acid amplification reaction mixture, said mixture comprising a plurality of different amplification templates, wherein said amplification templates comprise reverse transcription products from a plurality of RNA transcripts from a first gene expressing entity;
providing a second nucleic acid amplification reaction mixture, said mixture comprising a plurality of different amplification templates, wherein said amplification templates comprise reverse transcription products from a plurality of RNA transcripts from a second gene expressing entity;
subjecting said reaction mixtures to a PCR amplification regimen;
dispensing or withdrawing an aliquot from said first and said second reaction mixtures at plural stages during said amplification regimen;
separating and detecting nucleic acids in said aliquot, wherein said separating comprises capillary electrophoresis;
determining the quantity of a plurality of separated nucleic acid species in said aliquot,
for each said separated nucleic acid species from each said stage, correlating the quantity of said species with the stage at which said aliquot comprising said species was dispensed, thereby generating a transcriptional profile of said plurality of RNA transcripts expressed by said first and said second gene expressing entities; and
comparing said transcriptional profile from said first gene expressing entity with said transcriptional profile from said second gene expressing entity, wherein said comparing provides quantitative information regarding the abundance of said plurality of different amplification templates produced by said first and second entities.

55. A method of monitoring the amplification of a nucleic acid sequence, the method comprising:
providing a nucleic acid amplification reaction mixture comprising a template of said nucleic acid sequence;
performing a PCR amplification regimen on the mixture;
automatically dispensing an aliquot of said reaction mixture at plural stage intervals throughout the amplification regimen;
separating and detecting the nucleic acid species in said aliquot, wherein said separating comprises capillary electrophoresis; and,
for respective ones of plural separated species, determining the quantity of separated nucleic acid in said aliquot.

56. A method of determining the transcription profile of a nucleic acid sequence, the method comprising:
providing a nucleic acid amplification reaction mixture;
performing a PCR amplification regimen on the mixture;
dispensing an aliquot of said reaction mixture at plural stage intervals throughout the amplification regimen;
separating and detecting the nucleic acid species in said aliquot, wherein said separating comprises capillary electrophoresis; and,
for respective ones of plural separated species, determining the quantity of separated nucleic acid in said aliquot;
whereby a transcription profile is determined for said nucleic acid species, and wherein said profile provides quantitative information regarding the abundance, in said amplification reaction mixture, at the start of said amplification regimen, of said nucleic acid species.

57. A method of analyzing a nucleic acid amplification comprising:
providing a nucleic acid amplification reaction mixture comprising a plurality of different amplification templates;
subjecting said reaction mixture to a PCR amplification regimen;
dispensing or withdrawing an aliquot from said reaction mixture at plural stages during said amplification regimen;
separating and detecting nucleic acids in said aliquot, wherein said separating comprises capillary electrophoresis;
determining the quantity of a plurality of separated nucleic acid species in said aliquot,
for each said separated nucleic acid species from each said stage, correlating the quantity of said species with the stage at which said aliquot comprising said species was dispensed, and
calculating a threshold cycle for the amplification product of each of said plurality of different amplification templates, wherein said threshold cycle permits calculation of the abundance, at the start of said amplification regimen, of said plurality of different amplification templates in said amplification reaction mixture.

58. A method of analyzing the expression of a plurality of RNA transcripts between first and second gene expressing entities, said method comprising
providing a first nucleic acid amplification reaction mixture, said mixture comprising a plurality of different amplification templates, wherein said amplification templates comprise reverse transcription products from a plurality of RNA transcripts from a first gene expressing entity;
providing a second nucleic acid amplification reaction mixture, said mixture comprising a plurality of different amplification templates, wherein said amplification templates comprise reverse transcription products from a plurality of RNA transcripts from a second gene expressing entity;
subjecting said reaction mixtures to a PCR amplification regimen;
dispensing or withdrawing an aliquot from said first and said second reaction mixtures at plural stages during said amplification regimen;
separating and detecting nucleic acids in said aliquot, wherein said separating comprises capillary electrophoresis;
determining the quantity of a plurality of separated nucleic acid species in said aliquot,
for each said separated nucleic acid species from each said stage, correlating the quantity of said species with the stage at which said aliquot comprising said species was dispensed,
calculating a threshold cycle for the amplification product of each of said plurality of different amplification templates, wherein said threshold cycle permits calculation of the abundance, at the start of said amplification regimen, of said pluralities of different amplification templates in said first and second amplification reaction mixtures.

* * * * *